United States Patent [19]

Pike et al.

[11] 3,953,499

[45] Apr. 27, 1976

[54] 8,12-DIALKYL-PGE, AND PGF$_{1\alpha}$

[75] Inventors: John E. Pike; William P. Schneider, both of Kalamazoo, Mich.

[73] Assignee: The Upjohn Company, Kalamazoo, Mich.

[22] Filed: June 14, 1974

[21] Appl. No.: 479,238

Related U.S. Application Data

[60] Division of Ser. No. 313,368, Dec. 8, 1972, Pat. No. 3,888,919, which is a division of Ser. No. 123,370, March 11, 1971, abandoned, which is a continuation-in-part of Ser. No. 648,992, June 26, 1967, abandoned.

[52] U.S. Cl. ................... 260/514 D; 260/468 D
[51] Int. Cl.² .................. C07C 61/36; C07C 69/79
[58] Field of Search ...... 260/514 D, 468 D, 468 CA

[56] References Cited
UNITED STATES PATENTS 3,514,383  5/1970  Beal et al. ........................ 204/158

*Primary Examiner*—Robert Gerstl

[57] ABSTRACT

Prostaglandins E$_1$-type and F$_1$-type compounds of the formula

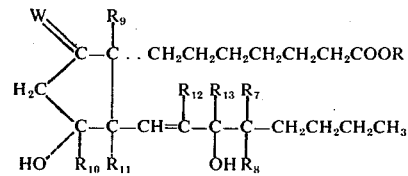

wherein R is hydrogen or a hydrocarbyl group containing from 1 to 12 carbon atoms, inclusive, wherein W is

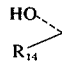

or O =, wherein R$_7$, R$_8$, R$_9$, R$_{10}$, R$_{11}$, R$_{12}$, R$_{13}$, and R$_{14}$ are hydrogen or alkyl of 1 to 4 carbon atoms, inclusive, provided (1) that at least one of R$_7$, R$_8$, R$_9$, R$_{10}$, R$_{11}$, R$_{12}$, R$_{13}$, and R$_{14}$ is alkyl (2) that when R$_{13}$ is alkyl, at least one of R$_7$, R$_8$, R$_9$, R$_{10}$, R$_{11}$, R$_{12}$, and R$_{14}$ is alkyl, and (3) that when R$_7$ is alkyl or thwn R$_7$ and R$_8$ are alkyl, at least one of R$_9$, R$_{10}$, R$_{11}$, R$_{12}$, R$_{13}$, and R$_{14}$ is alkyl; and the enantiomers and racemic mixtures thereof. These are useful for the same pharmacological purposes as the unsubstituted prostaglandins.

7 Claims, No Drawings

8,12-DIALKYL-PGE, AND PGF$_1\alpha$

CROSS REFERENCE TO RELATED APPLICATION

This application is a division of copending application Ser. No. 313,368, filed Dec. 8, 1972, now U.S. Pat. No. 3,888,919, which is a division of copending application Ser. No. 123,370, filed Mar. 11, 1971, and now abandoned, which is a continuation-in-part of copending application Ser. No. 648,992, filed June 26, 1967, and now abandoned.

BRIEF SUMMARY OF INVENTION

This invention relates to racemic and optically active prostaglandin analogs of the formula

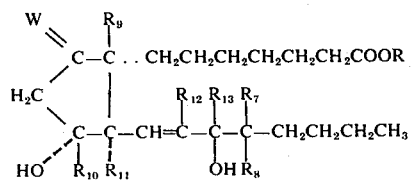

wherein R is hydrogen or a hydrocarbyl group containing from 1 to 12 carbon atoms, inclusive, wherein W is

or O =, wherein $R_7$, $R_8$, $R_9$, $R_{10}$, $R_{11}$, $R_{12}$, $R_{13}$, and $R_{14}$ are hydrogen or alkyl of 1 to 4 carbon atoms, inclusive, provided (1) that at least one of $R_7$, $R_8$, $R_9$, $R_{10}$, $R_{11}$, $R_{12}$, $R_{13}$, and $R_{14}$ is alkyl (2) that when $R_{13}$ is alkyl, at least one of $R_7$, $R_8$, $R_9$, $R_{10}$, $R_{11}$, $R_{12}$, and $R_{14}$ is alkyl, and (3) that when $R_7$ is alkyl or when $R_7$ and $R_8$ are alkyl, at least one of $R_9$, $R_{10}$, $R_{11}$, $R_{12}$, $R_{13}$, and $R_{14}$ is alkyl; and the enantiomers and racemic mixtures thereof; from unsaturated fatty acids of the formula

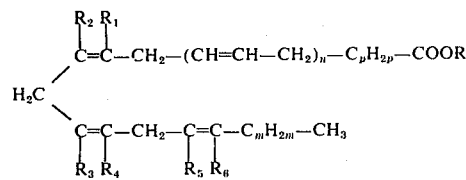

wherein R is H or hydrocarbyl, $R_1$, $R_2$, $R_3$, $R_4$, $R_5$, and $R_6$ are H or $CH_3$, m is an integer from 1 to 7, inclusive, n is 0 to 1, and p is an integer from 1 to 7, inclusive; and processes for preparing them, for example by oxidation with singlet oxygen to form peroxide intermediates followed by reduction or disproportionation of the peroxide intermediate, or by biological oxidation.

The compounds of this invention and processes for their production can be represented by the following sequence of formulas:

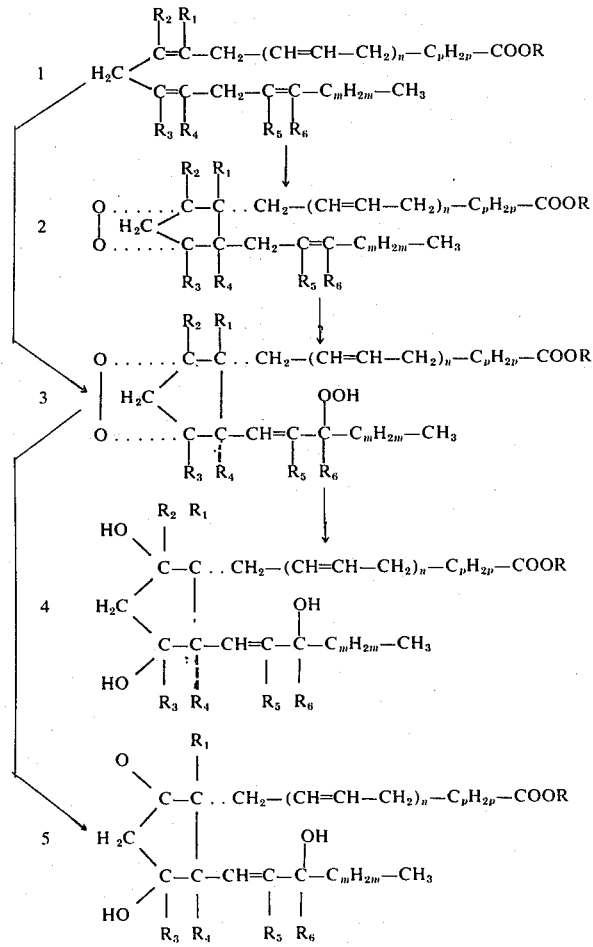

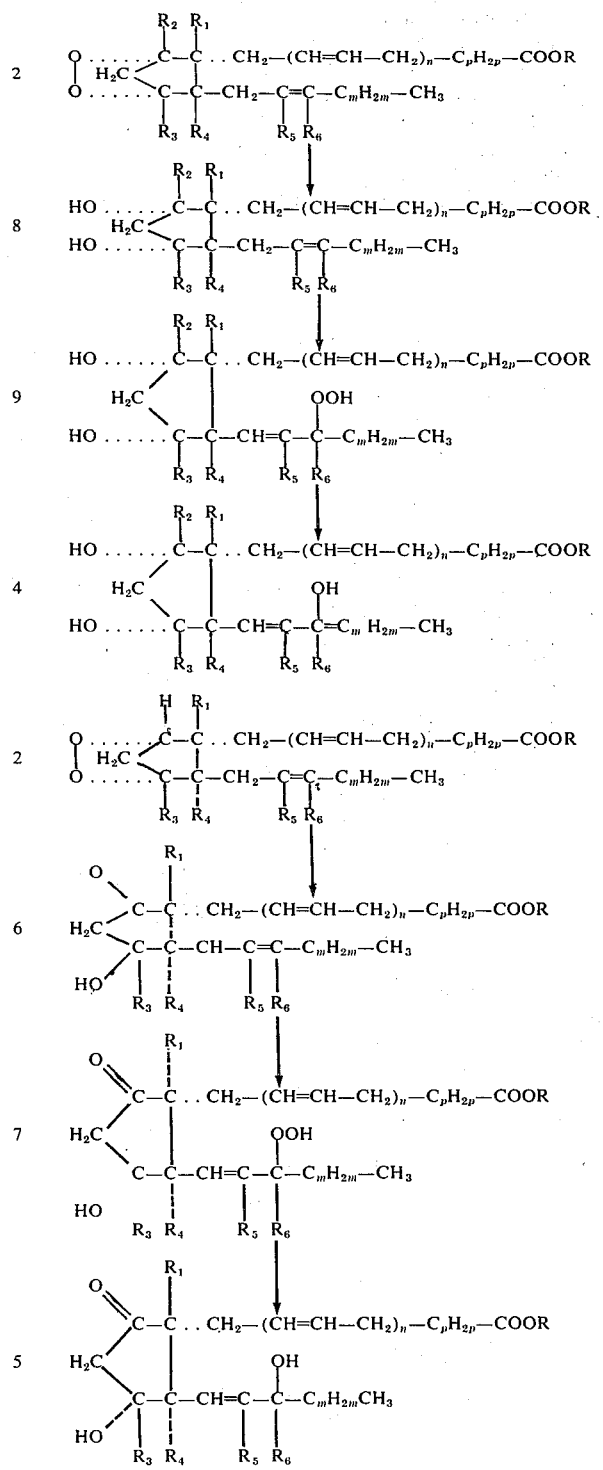

wherein R, $R_1$, $R_2$, $R_3$, $R_4$, $R_5$, $R_6$, $m$, $n$ and $p$ are as given above.

In the process of this invention all the compounds having one or more assymmetric carbon atoms can be produced as racemic mixtures. Those racemic mixtures which are obtained can be resolved at appropriate stages by methods well known in the art.

It is to be understood that the pictorial representation of the compounds in the flow sheet above is to be construed as inclusive of other forms including enantiomers and racemates, and not to be construed as limited to the particular form shown. The starting materials for the process of this invention are unsaturated fatty acids of formula 1. Many acids of this formula occur naturally, for example linolenic, bis-homo-γ-linolenic, and arachidonic acids. The natural acids, and the acids of formula 1 which do not occur in nature, can be prepared by synthetic methods, for example as shown by Osbond, Progress in the Chemistry of Fats and Other Lipids, Vol. 9, p. 121, 1966, and in the preparations below.

The process of this invention comprises the following:

The compounds of formula 1, for example bis-homo-γ-linolenic acid, are treated with singlet oxygen to produce a mixture of the compounds of formulas 2 and 3, for example racemic 7-[3α,5α-peroxy-2β-(2-octenyl)-cyclopent-1α-yl]heptanoic acid (2) and racemic 7-[3α,5α-peroxy-2β-(3-hydroperoxy-1-octenyl)-cyclopent-1α-yl]heptanoic acid (3). The relative proportions of compounds 2 and 3 will vary depending upon the substrate, the reaction conditions, and the amount of oxidant. A small excess of oxidant and mild reaction conditions will favor the production of compounds of formula 2 and a larger excess of oxidant and more severe conditions will result in the formation of mostly compounds of formula 3. The oxygenated products of structures 2 and 3 can be isolated by methods known to be useful in the isolation of products obtained by photochemical oxidations. In many instances it is preferred not to isolate these intermediate peroxy compounds but to transform the product in situ to the subsequent oxygenated products of this invention. Compounds 2 and 3 can be separated by means known in the art, for example by chromatography over acid washed silica gel, chromatography over silver-nitrate impregnated silica gel, preparative thin layer chromatography, and the like. The compounds of formula 2 can be transformed to the compounds of formula 3 by repeating the oxidation with singlet oxygen.

The use of singlet oxygen as a selective chemical reagent is known in the art. A number of methods are available for generating singlet oxygen, for example: 1) Photo-oxygenation in the presence of a photosensitizer such as chlorophyll, hematoporphyin, Rose Bengal, eosin and the like, as described by A. Nickon and W. L. Mendelson, J. Am. Chem. Soc. 87, 3921 (1965) and K. Gollnick and G. O. Schenk, Pure and Applied Chem., 9, 507 (1964), or as described in U.S. Pat. No. 3,281,415. 2) Electrodeless discharge of gaseous oxygen, as described by E. J. Corey and W. C. Taylor, J. Am. Chem. Soc. 86, 3881 (1964). 3) Use of hypochlorites and hydrogen peroxide. This method is described by C. S. Foote and S. Wexler, J. Am. Chem. Soc. 86, 3879 and 3881 (1964), and in U.S. Pat. No. 3,274,181. 4) Use of the benzyl cyanide; hydrogen peroxide; base system, described by E. McKeown and W. A. Waters, Nature, 203, 1063 (1964). 5) Use of hydrogen peroxide and oxalyl chloride, as described by E. A. Chandross, Tetrahedron Letters, 12,761 (1963), and Corey, cited above. 6) Use of ozone and phosphines, phosphites, etc, as given by Q. E. Thompson, J. Am. Chem. Soc. 83, 845 (1961) and Corey, cited above. 7) By the reaction of hydrogen peroxide in aqueous solution with $Fe^{++}$, T (III), or Ce (IV) ions, described by Stauff and Lohman, Z. physikal Chem., N. F., 40, 123 (1964) and 8) By pyrolysis of aromatic endoperoxides, such as anthracene or tryptycene endoperoxide. The 9,10-diarylanthracene endoperoxides are especially useful.

In all the reaction mixtures described above, addition of autoxidation inhibitors results in improved results in the process of this invention, by decreasing autoxidation side reactions with ordinary oxygen. Suitable antioxidants are phenol, hydroquinone, vitamin E, 2,6-di-t-butyl-phenol and, preferably, 2,6-di-t-butyl-4-methyl-phenol.

In some cases it is advantageous to add a metal salt as a catalyst for the singlet oxygen oxidation. Suitable metal ions are $Cu^+$, $Cu^{++}$, $CO^{++}$, $Fe^{++}$, $Pd^{++}$, $Pt^{++}$, $Rh^{+++}$, $Ru^{+++}$, $Ag^+$, $Fe^{+++}$, $Cz^{++}$, $Zn^{++}$, $Ce^{+++}$, $Ce^{++++}$, and $Ti^{+++}$. These salts can, for example, be chlorides, bromides, sulfates, nitrates, and the like.

The compounds of formula 3, for example racemic 7-[3α,5α-peroxy-2β-(3-hydroperoxy-1-octenyl)cyclopent-1α-yl]heptanoic acid, are transformed to the compounds of formula 4, for example, racemic 7-[3α,5α-dihydroxy-2β-(3-hydroxy-1-octenyl)cyclopent-1α-yl]heptanoic acid (racemic PGF1α), by mild reduction. Suitable reducing agents are metal hydrides, for example sodium and potassium borohydrides, thiourea, sodium sulfite, zinc dust and acetic acid, hydrogen in the presence of a catalyst, triphenylphosphine, and the like. An excess of reducing agent is ordinarily employed, and appropriate solvents and temperatures are employed as well known in the art for the use of these reducing agents.

Very mild reduction of compounds of formula 3 results in the reduction of the hydroperoxy group on the side chain without destroying the peroxy ring compound, giving compounds designated 3α, for example racemic 7-[3α,5α-peroxy-2β-(3-hydroxy-1-octenyl)cyclopent-1α-yl]heptanoic acid (3α) is obtained from racemic 7-[3α,5α-peroxy-2β-(3-hydroperoxy-1-octenyl)cyclopent-1α-yl]heptanoic acid (3). This selective reduction can be obtained using about one equivalent, or a small excess over one equivalent, of the reducing agents named for the reduction of compound 3 to compound 4, or by the use of an alkali metal iodide and sodium thiosulfate as a reducing agent. The resulting peroxy compounds can be isolated as described above for compounds of formulas 2 and 3, or can be carried through the next step in situ. The compounds designated 3α (wherein $R_2$ is hydrogen) on treatment with a slightly basic chromatographic alumina, or a mild base such as pyridine, potassium acetate in ethanol and the like, are converted to compounds of formula 5, for example racemic 7-[3α-hydroxy-5-oxo-2β-(3-hydroxy-1-octenyl)cyclopent-1α-yl]heptanoic acid (5) (racemic $PGE_1$). The conversion of the compounds designated 3 to the compounds of formula 5 can also be carried out by the action of heat, by irradiation with ultraviolet light, and by the action of titanous chloride in the presence of an acidic catalyst as shown by Paget, J. Chem. Soc. 829 (1938) and Davis et. al., Proc. Chem. Soc. 83 (1961).

Alternatively the compounds of formulas 4 and 5 can be prepared from the compounds of formula 2 by first reducing or isomerizing the peroxide ring, and then introducing the side chain hydroxyl group. Treating compounds of formula 2, for example racemic 7-[3α,5α-peroxy-2β-(2-octenyl)cyclopent-1α-yl]-heptanoic acid, with a reducing agent as described above for the conversion of compounds of formula 3 to the compounds of formula 4 produces compounds of formula 8, for example racemic 7-[3α,5α-dihydroxy-2β-(2-octenyl)cyclopent-1α-yl]heptanoic acid (8). Treating compounds of formula 8 with singlet oxygen as described above for the conversion of compounds of formula 2 to the compounds of formula 3, produces compounds of formula 9, for example racemic 7-[3α,5α-di-hydroxy-2β-(3-hydroperoxy-1-octenyl)cyclopent-1α-yl]heptanoic acid, which are then treated with a reducing agent, in the manner described above for the production of compounds of formula 4 from compounds of formula 3, to produce compounds of formula 4, for example racemic 7-[3α,5α-dihydroxy-2β-(3- hydroxy-1-octenyl)-cyclopent-1α-yl]-heptanoic acid (4). Treating compounds of formula 2 wherein R₂ is hydrogen with a base or another isomerizing agent as described above for the production of the compounds of formula 5 from the compounds designated 3α produces the compounds of formula 6, for example racemic 7-[3α-hydroxy-5-oxo-2β-(2-octenyl)cyclopent-1α-yl]heptanoic acid (6). Treating compounds of formula 6 with singlet oxygen as described above for the conversion of compounds of formula 2 to the compounds of formula 3 produces compounds of formula 7, for example racemic 7-[3α-hydroxy-5-oxo-2β-(3-hydroperoxy-1-octenyl)cyclopent-1α-yl]heptanoic acid (7), which are then treated in the manner described above for the production of compounds of formula 4 from the compounds of formula 3 with a reducing agent to produce compounds of formula 5, for example racemic 7-[3α-hydroxy-5-oxo-2β-(3-hydrox-1-octenyl)cyclopent-1α-yl]heptanoic acid (5).

All of the compounds of this invention can be isolated and purified by conventional methods. Isolation can be accomplished, for example, by dilution of the reaction mixture with water, extraction with a water-immiscible solvent, such as methylene chloride, ethyl acetate, benzene, cyclohexane, ether, toluene and the like, chromatography, adsorption on ion-exchange resins, distillation, or a combination of these. Purification of the compounds of this invention can be accomplished by means known in the art for the purification of prostaglandins and lipids, fatty acids, and fatty esters, for example reverse phase partition chromatography, countercurrent distribution, adsorption chromatography on acid washed Florisil (synthetic magnesium silicate) and acid washed silica gel, preparative paper chromatography, preparative thin layer chromatography, chromatography over silver loaded cation exchange resins, and combinations thereof can be used effectively to purify the compounds produced by the processes of this invention.

The starting unsaturated fatty acids may, if desired, be esterified and the esters can be carried through the steps of the invention as shown in the flowsheet above, except in those singlet oxygen processes involving alkaline reaction conditions. The compounds of formulas 4, 5, 6 and 8 can also be esterified. The esterification is preferably carried out by reacting the selected acid with a diazoalkane, e.g. diazomethane, diazoethane, diazobutane, 1-diazo-2-ethylhexane, cyclohexyldiazomethane, diazododecane, and the like, in the presence of an inert organic solvent such as methanol, diethyl ether, tetrahydrofuran and the like at about 0° to 50° C.

The racemic products and intermediates of this invention can be resolved into their optically active components by a number of methods of resolution well known in the art. For example, the free acids can be treated with an optically active base such as cinchonine, quinine, brucine, d- or l-α-phenylethylamine and the like to produce diastereoisomeric salts which can be separated by crystallization. Alternatively the acid may be esterified with an optically active alcohol and the products resolved. Resolution can also be accomplished by selective transformation of one isomer with a biologically active prostaglandin transforming system, for example, the 15-dehydrogenating system present in lung such as guinea pig, rat and pig lung and in microorganisims such as fungi. Such transformations can be carried out by incubation or perfusion using methods well established in the art, followed by isolation and recovery of both the isomer resistant to the metabolic transformation applied and the product formed by the enzymatic transformation.

The process of this invention produces racemic prostaglandins corresponding otherwise to natural prostaglandins when bis-homo-γ-linolenic acid or arachiodonic acid are used as the starting material, and derivatives or analogs of the natural prostaglandins when other unsaturated acids of formula 1 are used as starting materials.

The prostaglandins are a family of closely related compounds which have been obtained from various animal tissues, and which stimulate smooth muscle, lower arterial blood pressure, antagonize epinephrine-induced mobilization of free fatty acids, and have other pharmacological and autopharmacological effects in mammals, including man. Se Bergstrom et al., J. Biol. Chem. 238, 3555 (1963), Horton, Experientia, 21, 113 (1965), and references cited in those for discussions of the occurrence, structure, and properties of the prostaglandins.

All of the so-called natural prostaglandins are derivatives of prostanoic acid:

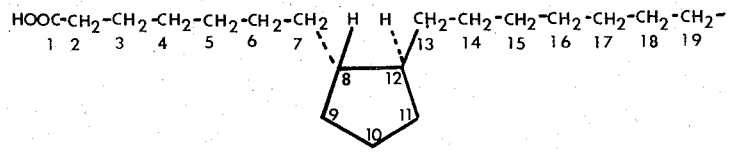

10

The hydrogen atoms attached to C-8 and C-12 in formula 10 are in trans configuration, and the stereochemistry at C-8 and C-12 is indicated in accord with Nugteren et al., Nature, 212, 38 (1966).

One significant characteristic of these natural prostanoic acid derivatives is the length of the multi-carbon side chains attached to C-8 and to C-12. In prostanoic acid and in each of the prostaglandins obtained from animal tissues, the chain attached to C-8 always contains seven carbon atoms and the chain attached to C-12 always contains eight carbon atoms.

The compounds of formulas 4 and 5 in which the length of the side chains corresponds to the side chains of prostanoic acid exhibit hypotensive and smooth muscle stimulating activity. The hypotensive activity of these compounds makes them useful in the control of hypertension in birds and mammals, including humans and valuable domestic animals, and in laboratory animals such as rats, mice, and rabbits. They also possess activity as fertility controlling agents, central nervous system regulatory agents, salt- and water-retention regulatory agents, fat metabolic regulatory agents and as serum cholesterol lowering agents which latter activity makes these compounds useful in prevention of the onset of atherosclerosis and also in the treatment thereof in birds and mammals, including humans and valuable domestic animals. The activity of said compounds as fat regulatory agents makes them useful in the control of obesity.

The compounds of formulas 4 and 5 which are analogs or derivatives of the natural prostaglandins have prostaglandin like activity which includes but is not limited to smooth muscle stimulation, vasodepressor activity, and inhibition of triglyceride breakdown in adipose tissues.

In comparison with the natural prostaglandins, the analogs and derivatives of this invention are substantially more specific in causing prostaglandin-like biological responses, and their use for desired pharmacological purposes results in substantially smaller and/or fewer undesired side effects. Therefore, the prostaglandin analogs and derivatives of this invention are useful as harmacological agents for pharmacological control of hypertension, to block mobilization of free fatty acids, and to stimulate smooth muscle in mammals, including man, valuable domestic animals, and laboratory animals.

Compounds of formulas 4 and 5, wherein one or more of the groups $R_1$, $R_2$, $R_3$, $R_4$, $R_5$, and $R_6$ is an alkyl radical of 1 to 4 carbon atoms, inclusive, rather than hydrogen, or wherein 1 to 2 alkyl radicals of 1 to 4 carbon atoms, inclusive, are present in $C_mH_{2m}$ adjacent to the side chain C-OH, especially compounds so substituted and wherein the lengths of the two main side chains are the same as for prostanoic acid, have unexpectedly decreased rates of metabolic destruction and consequently longer durations of the desired activity. In addition these particular compounds are substantially and unexpectedly more specific in causing desired prostaglandin-like biological responses and their use for pharmacological purposes results in substantially smaller and/or fewer undesired side effects.

The compounds of formulas 4 and 5 can be administered orally, parenterally, or intravenously. For example, a compound can be administered by intravenous infusion of a sterile isotonic saline solution at the rate of about 0.01 to about 10, preferably about 0.05 to about 5, micrograms per kilogram of animal body weight per minute.

The products and intermediates of this invention when produced by singlet oxygen oxidation of unsaturated fatty acids, as described above, are racemic mixtures. Optically active products and intermediates can be obtained by resolution of these mixtures, as described above. In addition, the optically active products 4 and 5, with the configuration shown in the flowsheet above, are produced by biological oxidation of the starting materials of formula 1 following the procedures given in U.S. Pat. No. 3,290,226 or U.S. Pat. No. 3,296,091. For example, the novel branched chain prostaglandins 7-[3α-hydroxy-5-oxo-2β-(4-methyl-3-hydroxy-1-octenyl)-cyclopent-1α-yl]heptanoic acid, 7-[3α,5α-dihydroxy-2β-(4-methyl-3-hydroxy-1-octenyl)-cyclopent-1α-yl]heptanoic acid, 7-[3α-hydroxy-5-oxo-2β-(4,4-dimethyl-3-hydroxy-1-octenyl)-cyclopent-1α-yl]heptanoic acid, 7-[3α,5α-dihydroxy-2β-(4,4-dimethyl-3-hydroxy-1-octenyl)-cyclopent-1α-yl]heptanoic acid, 7-[3α-hydroxy-5-oxo-2β-(3-hydroxy-3-methyl-1-octenyl)-cyclopent-1α-6l]heptanoic acid, 7-[3α,5α-dihydroxy-2β-(3-hydroxy-3-methyl-1-octenyl)cyclopent-1α-yl]heptanoic acid, 7-[3α-hydroxy-3β-methyl-5-oxo-2β-(3-hydroxy-3-methyl-1-octenyl)-cyclopent-1α-yl]heptanoic acid, 7-[3α,5α-dihydroxy-3β-methyl-2β-(3-hydroxy-3-methyl-1-octenyl)-cyclopent-1α-yl]heptanoic acid, 7-[3α-hydroxy-1β,2α-dimethyl-5-oxo-2β-(3-hydroxy-1-octenyl)-cyclopent-1α-yl]heptanoic acid and 7-[3α,5α-dihydroxy-1β,2α-dimethyl-2β-(3-hydroxy-1-octenyl)-cyclopent-1α-yl]heptanoic acid are obtained by substituting the corresponding branched chain unsaturated fatty acids, 16-methyl-8,11,14-e.cosatrienoic acid, 16,16-dimethyl-8,11,14-eicosatrienoic acid, 15-methyl-8,11,14-eicosatrienoic acid, 11,15-dimethyl-8,11,14-eicosatrienoic acid, and 3,12-dimethyl-8,11,14-eicosatrienoic acid for arachiodonic acid in Example 1 of U.S. Patent 3,290,226 or Example 1 of U.S. Pat. No. 3,296,091.

DETAILED DESCRIPTION

In the examples which follow, the progress of the reaction and the purification procedures can advantageously be followed by thin layer chromatographic analysis. A preferred procedure is to use silica gel plates developed with ethyl acetate and sprayed with sulfuric acid to detect the spots.

In some of the preparations which follow, nuclear magnetic resonance spectroscopy (N.M.R.) has been used to characterize and define the products obtained. All N.M.R. data were obtained on the Varian N.M.R. instrument, Model A-60 (run at 60 megacycles) and reported in cycles per second (cps) downfield from the standard tetramethylsilane.

Preparation 1

Cis,cis,cis-9,12,15-heneicosatrienoic acid.

A. 1-Bromo-6-chlorohexane

Following the procedure of Cloke, et al., J. Am. Chem. Soc. 53, 2794 (1931), hexamethylene chlorohydrin was converted to 1-bromo-6-chlorohexane, b.p. 66°–68°C./1mm., $N^{25}=1.4795$.

Anal. Calc'd. for $C_6H_{12}BrCl$: C, 36.11, H, 6.06. Found: C, 37.11; H, 6.05.

B. 8-Chloro-1-octyne

To about 450 ml. of liquid ammonia saturated with acetylene was added slowly 15.5 g. of sodium with continued addition of acetylene so that the solution remained colorless. After all the sodium had dissolved addition of acetylene was ended and the acetylene delivery tube was removed, then a dry-ice acetone condensor was fitted and 135 g. of 1-bromo-6-chlorohexane was added dropwise. The ammonia refluxed vigorously during the addition of the 1-bromo-6-chlorohexane. After the addition was completed the mixture was stirred for 2 hours, then 200 ml. water was added slowly and the mixture was allowed to warm to room temperature and extracted with ether. The ether extract was washed with water, 3N hydrochloric acid, and aqueous sodium bicarbonate, then was dried over sodium sulfate and evaporated to leave a residue which was distilled under reduced pressure. The major fraction collected, 84 g., comprised 8-chloro-1-octyne boiling at 60°–65°C./10 mm. and showing infrared absorption maxima at 3270, 2120 and 735 $cm^{-1}$.

Anal. Calc'd. for $C_8H_{13}Cl$: C, 66.43; H, 9.06; Cl, 24.52. Found: C, 65.53; H, 8.60; Cl, 25.07.

C. 1-Chloro-7,10,13-nonadecatrlyne

To 13.3 ml. of 3M ethyl magnesium bromide in 30 ml. of dry tetrahydrofuran was added a solution of 5.8 g. of 8-chloro-1-octyne in 10 ml. of dry tetrahydrofuran. The mixture was refluxed under nitrogen for 30 min., then stirred at room temperature (about 25°C.) for 30 min., and 0.25 g. of powdered dry cupious chloride was added. The mixture was stirred for 20 minutes, then a solution of 8.98 g. of 1-bromo-2,5-undecadiyne in 10 ml. of dry tetrahydrofuran was added, and the reaction mixture was stirred and heated under reflux for 10 hrs., during which a yellow precipitate formed. The entire mixture was poured into saturated aqueous ammonium chloride and ether, filtered through Celite (diatomaceous earth filter aid), and the ether solution was separated, washed with water, dried over sodium sulfate, and evaporated to give a residue comprising 1-chloro-7,10,13-nonadecatriyne. The thus obtained residue was distilled in a short path distillation flask up to 150°/0.005 mm. to remove starting materials, then was distilled in a short path tube, bath temperature up to 190°/0.004 mm. to give 1-chloro-7,10,13-nonadecatrivne as a yellow oil, which crystallized when stored at −10°C., and had the following analysis:

I.R. (principal bands): 1315, 1220 and 730 cm$^{-1}$.

N-M-R.: 212 cps. (triplet J=7 cps.), 187.5 cps., (quintet J=2.5 cps.), 130 cps. (multiplet) 54 cps. (triplet J=6 cps).

D. 1-Chloro-cis,cis,cis-7,10,13-nonadecatriene

A mixture of 35.9 g. of 1-chloro-7,10,13-nonadecatriyne dissolved in 200 ml. of pyridine and 5.4 g. of 5% palladium on barium sulfate was shaken in an atmosphere of hydrogen in a Parr hydrogenator for 1.25 hrs. (pressure drop 21.5 lb.; 0.1 mole hydrogen = 8.5 lb.), then the reaction mixture was poured into water and extracted with ether. The ether extract was washed several times with water, then with dilute hydrochloric acid, followed by saturated aqueous sodium chloride. The ether solution was then dried over sodium sulfate, and evaporated under reduced pressure leaving a residue comprising 1-chloro-cis,cis,cis-7,10,13-nonadecatriene which was further purified by distillation on a shaking short path distillation apparatus, giving 27 g. of 1-chloro-cis,cis,cis-7,10,13--nonadecatriene collected at a jacket temperature of 180°-190°/0.005 mm.

Anal. Calc'd. for $C_{19}H_{33}Cl$: C, 76.85; H, 11.20; Cl, 11.94. Found: C, 76.38; H, 12.98; Cl, 11.88.

E. Cis,cis,cis-9,12,15-heneicosatrienoic acid

To 15 ml. of n-butanol under nitrogen was added 211 mg. of sodium in pieces. The mixture was heated gently until all the sodium had dissolved, then 1.2 ml. of diethylmalonate was added and the mixture was refluxed one hour, then cooled, and a solution of 2.0 g. of 1-chloro-cis,cis,cis-7,10,13-nonadecatriene in 7.5 ml. of n-butanol was added. The resulting reaction mixture was refluxed for 3 hrs. under nitrogen, then allowed to stand for about 20 hrs., and concentrated under reduced pressure. The thus obtained residue was dissolved in a solution of 1.9 g. of potassium hydroxide in 38 ml. of 95% ethanol and heated under reflux for 3.5 hrs., then was concentrated to about ⅓ volume, diluted with water, and extracted with ether. The ether solution was extracted with 1N aqueous sodium hydroxide. The sodium hydroxide solution was made acid with 3N hydrochloric acid and extracted twice with ether. The ether extracts were washed with water, then with saturated aqueous sodium chloride, dried over sodium sulfate, and evaporated to give 1.72 g. of a pale yellow oil. The thus obtained oil was heated in a short path distillation tube at 140°C. under reduced pressure until decarboxylation was complete, then was distilled at a bath temperature of 180°-200°/0.006 mm., thus obtaining a distillate comprising cis,cis,cis-9,12,15-heneicosatrienoic acid.

Preparation 2

15-methyl-8,11,14-eicosatrienoic acid

A. 3-Hydroxy-3-methyl-1-octyne

A solution of 46.5 g of 2-heptanone in 56 ml. of tetrahydrofuran was added slowly, with stirring, to a mixture of 45.5 g. of lithium acetylide - ethylene diamine, 200 ml. of dry tetrahydrofuran and 200 ml. of benzene at 35°C. under nitrogen. Stirring was continued for 2.5 hrs. after addition of the 2-heptanone was completed, then 130 ml. of water was added slowly and the mixture was heated under reflux for 1 hour. The mixture was cooled and extracted with ether. The ether extract was washed with water, 1N hydrochloric acid, aqueous sodium bicarbonate, saturated aqueous sodium chloride, dried over $Na_2SO_4$, and evaporated. The thus obtained residue was distilled through a Vigreaux column, giving 36 g. of 3-hydroxy-3-methyl-1-octyne having a boiling point of 85°-90°C. at 28″ of mercury.

B. 3-Hydroxy-3-methyl-1-octene

A mixture of 20 g. of 2-hydroxy-2-methyl-1-octyne, 500 mg. of 5% palladium on barium sulfate catalyst, and 200 ml. of pyridine was shaken under hydrogen, at an initial pressure of 45 lb./sp. in. at room temperature (about 25°C.). The hydrogenation was stopped after 20 min., at which time the pressure drop corresponded to the calculated amount for 1 mole of hydrogen uptake per mole of compound. The reaction mixture was poured into water and extracted with ether. The ether extract was washed with water, dilute hydrochloric acid, aqueous bicarbonate, dried over sodium sulfate, and evaporated. The thus obtained residue was distilled through a Vigreaux column and 15.5 g. of distillate comprising 3-hydroxy-3-methyl-1-octene having a boiling point of 89°-90°C. at 28″ of mercury was collected.

Anal. Calc'd. for $C_9H_{18}O$: C, 75.99; H, 12.76. Found: C, 75.56; H, 12.82.

C. 1-Bromo-3-methyl-2-octene

In an ice-salt bath 25 ml. of 48% hydrobromic acid was saturated with hydrogen bromide by bubbling through for 5-10 minutes, then 10 g. of 3-hydroxy-3-methyl-1-octene was added slowly with stirring. The mixture was stirred an additional 20 min. then benzene was added and the benzene layer was separated, washed with ice water, aqueous sodium bicarbonate, saturated aqueous sodium chloride, dried over sodium sulfate, and evaporated to give a residue. The thus obtained residue was distilled through a Vigreaux column, collecting a main fraction weighing 11 g. comprising 1-bromo-3-methyl-2-octene boiling at 95°-110°C. at 28″ of mercury.

Anal. Calc'd for $C_{19}H_{17}Br$: C, 52.69; H, 8.35; Br, 38.95. Found: C, 52.58; H, 8.40; Br, 38.59.

D. 6-Methylundec-2-yn-5-en-1-ol

A solution of 5.6 g. of propargyl tetrahydropyranyl ether in 40 ml. of dry tetrahydrofuran was added slowly, with stirring to 14 ml. of 3 M ethyl magnesium bromide in ether under nitrogen. The mixture was heated under reflux for 1 hr., then was cooled and 120 mg. of powdered cuprous chloride was added. After stirring for 20 mins., a solution of 8.0 g. of 1-bromo-3- methyl-2-octene in 8ml. of tetrahydrofuran was added. The mixture was heated under reflux for 2 hrs., then cooled, and 20 ml of saturated aqueous ammonium chloride was added slowly. Ether was added, and the mixture was filtered through Celite (diatomaceous earth filter aid), then the ether layer was separated, washed with water, dried over sodium sulfate, and evaporated giving a residue. The thus obtained residue was heated under reflux for two hours in 24 ml. of methanol containing 148 mg. of p-toluene-sulfonic acid, then the mixture was cooled, diluted with water, and extracted with ether. The ether extract was washed with aqueous sodium bicarbonate, aqueous saturated sodium chloride, dried over sodium sulfate, and evaporated leaving a residue. The residue was distilled and gave 4.0 g. of a mixture comprising 6-methylundec-2-yn-5-en-1-ol, b.p. 96°–101°C./0.006 mm.

E. 1-Bromo-6-methylundec-2-yn-5-ene

A mixture of 17 g. of 6-methylundec-2-yn-5-en-1-ol, 32.4 ml. of ether, and 2.07 ml. of pyridine was stirred under nitrogen in an ice-salt bath and 4.5 ml. of phosphorus tribromide was added. The ice-salt bath was then removed and the mixture was first allowed to warm to room temperature, then was heated under reflux for 2.5 hrs. The mixture was again cooled in an ice bath, and 15 ml. each of ether and water were added. The ether layer was separated, washed with aqueous sodium bicarbonate, saturated aqueous sodium chloride, dried over sodium sulfate, and evaporated. The thus obtained residue was distilled, collecting 14 g. of a mixture comprising 1-bromo-6-methylundec-2-yn-5-ene at 85°–89°C./0.005 mm.

F. 1-Chloro-14-methyl-nonadeca-7,10-diyn-13-ene

To 21 ml. of 3M ethereal methyl magnesium bromide in 47.5 ml. of dry tetrahydrofuran under nitrogen was added 9.2 g. of 1-chloro-7-octyne in 15 ml. of tetrahydrofuran. The mixture was heated under reflux for 30 min., then was allowed to cool to room temperature during another 30 minutes after which 365 mg. of cuprous chloride was added. The mixture was heated under reflux for 20 min., then a solution of 14 g. of 1-bromo-6-methyl-undec-2-yn-5-ene in 12.9 ml. of tetrahydrofuran was added. The mixture was heated under reflux for 10 hrs. then cooled in an ice bath and 250 ml. saturated aqueous ammonium chloride was added. Ether was added and the mixture was filtered through Celite (diatomaceous earth filter ald) and separated. The thus obtained ether layer was washed with saturated aqueous sodium chloride, dried with magnesium sulfate, and evaporated. The thus obtained residue was distilled through a rocking short-path distillation apparatus, collecting 11.5 g. of a mixture comprising 1-chloro-14-methylnonadeca-7,10-dlyn-13-ene at a bath temperature of 180°–190°/0.005 mm.

Anal. Calc'd. for $C_{20}H_{21}Cl$: Cl, 11.55. Found: Cl, 12.59

F. 1-Chloro-14-methyl-7,10,13-nonadecatriene

A mixture of 11.0 g. of 1-chloro-14-methyl-nonadeca-7,10-diyn-13-ene, 1.5 g. of 5% palladium on barium sulfate, and 80 ml. of pyridine was shaken in a Parr rocker under 40 lb. of hydrogen pressure for about 1.3 hrs., at which time two moles of hydrogen had been absorbed. The reaction mixture was then poured into water and extracted with ether. The extract was washed with water, dilute hydrochloric acid, saturated aqueous sodium chloride, dried over sodium sulfate, and evaporated leaving a residue comprising 1-chloro-14-methyl-7,10,13-nonadecatriene. The residue was distilled in a rocking short-path distillation apparatus, collecting 7.6 g. of a mixture comprising 1-chloro-14-methyl-7,10,13-nonadecatriene at a bath temperature of 180°C. and a pressure of 0.005 mm.

G. Methyl 15-methyl-8,11,14-eicosatrienoate

A mixture of 7.5 g. of 1-chloro-14-methyl-7,10,13-nonadecatriene, 7.5 g. of potassium cyanide, and 36.8 ml. of dimethyl-sulfoxide was stirred and heated under nitrogen for 2.5 hrs. at 115°C. The mixture was then poured into water and extracted with ether. The ether extract was washed with water, saturated aqueous sodium cloride, dried over sodium sulfate, and evaporated leaving a residue. The thus obtained residue was cooled in an ice bath and mixed with 54 ml. of 25% hydrogen chloride in methanol containing 0.6 ml. of water. The ice was allowed to melt and the mixture was stirred for about 18 hrs., then was poured into water and extracted with ether. The ether extract was washed with water, aqueous sodium bicarbonate, saturated aqueous sodium chloride, dried over $Na_2SO_4$, and evaporated leaving a residue. The residue was distilled in a rocking short path distillation apparatus and a product comprising methyl 15-methyl-8,11,14-alcosatrienoate was collected at bath temperatures up to 220° at 0.5 to 0.05 mm. The above distillate was dissolved in cyclohexane and chromatographed over 250 g. of silica gel, eluting with 1 l. each of 2 ½%, 5% and 10% ethyl acetate in cyclohexane, collecting 100 ml. fractions. Fractions 14 to 18 were evaporated to give 6.80 g. of residue comprising methyl 15-methyl-8,11,14-eicosatrienoate.

H. 15-Methyl-8,11,14-elcosatrienoic acid

A mixture of 1.3 g. of methyl 15-methyl-8,11,14-eicosatrienoic acid, 12.8 ml of 95% ethanol, 1.1 g. of potassium hydroxide and 1.1 ml. of water under a nitrogen atmosphere was heated under reflux for 2hours, then water and Skellysolve "B" (mixed hexanes) were added. The aqueous and organic layers were separated and the aqueous layer was made acid with 3N hydrochloric acid, then extracted with ether. The ether extract was washed with water, then with saturated aqueous sodium chloride, dried over sodium sulfate, and evaporated leaving a residue comprising 15-methyl-8,11,14-eicosatrienoic acid. The residue was distilled in a short path tube at bath temperatures of about 180°C. and a pressure of about 0.007 mm. The distillate was dissolved in 5% ethyl acetate-benzene and chromatographed over 100 g. of acid washed silica gel. Elution with 600 ml. 5%, 500 ml. 10% and 200 ml. 25% ethyl acetate in benzene, then with 100 ml. of ethyl acetate, collecting 50 ml. fractions, and evaporation of the eluate fractions gave a first peak of 183 mg., followed by a 448 mg. peak comprising 15-methyl-8,11,14-eicosatrienoic acid showing one spot on TLC analysis, and having the following NMR absorptions:

singlet at 628 cps (COOH): multiplet at 322 cps

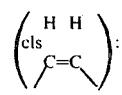

triplet at 167 cps. (diallylic -CH$_2$-) and triplet at 53 cps (CH$_3$-).

Preparation 3.

2-Methyl-8,11,14-elcosatrienoic acid

A. 1-Hydroxy-cis,cis,cis-6,9,12-octadecatriene

A solution of 50 g. of methyl γ-linolenate in 400 ml. of absolute ether is added dropwise with stirring to a suspension of 25.0 g. of lithium aluminum hydride in 1400 ml. of anhydrous ether under nitrogen. After addition is complete the mixture is stirred and heated under reflux for 6 hrs. The reaction mixture is then cooled with an ice bath, ard ethyl acetate is added dropwise with caution to decompose excess lithium aluminum hydride. Water is then added until the inorganic satls separate. and 20 g. of Celite (diatomaceous earth filter aid) is added. The mixture is then filtered through sodium sulfate, and the filtrate is dried over sodium sulfate. The ether solution is then evaporated under reduced pressure, giving 47.26 g. of a residue comprising 1-hydroxy-cis,cis,cis-6,9,12-octadecatriene and some unchanged starting material.

A solution of 75.0 g. of residue obtained as above is dissolved in 1640 ml of methanol and stirred under nitrogen, then a solution of 82 g. of potassium hydroxide in 100 ml. of water is added and the mixture is stirred at room temperature (about 23°C.) for about 18 hrs. About 50 ml. of water is added to the reaction mixture, and most of the methanol is removed by evaporation under reduced pressure. The mixture is then extracted three times with 500-ml. portions of methylene cloride. The methylene chloride extracts are combined and washed with water until the washings are neutral. The methylene chloride solution is then dried over sodium sulfate and evaporated under reduced pressure to give about 69.5 g. of 1-hydroxy-cis,cis,cis-6,9,12-octadecatriene.

B. 1-iodo-cis,cis,cis-6,9,12-octadecatriene

A solution of 28.0 g. of 1-hydroxy-cis,cis,cis-6,9,12-octadecatriene in 300 ml. of pyridine is cooled in an ice-salt bath and a solution of 45.0 g. of p-toluenesulfonyl chloride in 100 ml. of pyridine is added dropwise over a period of 30 minutes., then the ice-salt bath is removed and the reaction mixture is allowed to stand for 3 hrs. at room temperature. The mixture is then poured into 1 l. of ice and water, and hydrochloric acid is added carefully until the mixture is acidic. The mixture is then extracted 4 times with 200-ml. portions of methylene chloride, keeping the temperature at 0°C. by adding ice as needed. The methylene chloride extracts are combined and washed with 5% hydrochloric acid, then with saturated aqueous sodium bicarbonate, and with water until the washings are neutral. The methylene chloride solution is then dried over sodium sulfate and evaporated under reduced pressure to give about 35 g. of a residue comprising 1-hydroxy-cis,cis,cis-6,9,12-octadecatriene p-toluenesulfonate. The thus obtained p-toluenesulfonate is dissolved in 1 l. of acetone and stirred under nitrogen, then 60 g. of powdered sodium iodide is added and the mixture is stirred and heated under reflux for 4 hrs. The mixture is cooled and filtered to remove precipitated sodium p-toluenesulfonate. The precipitate is washed with 200 ml. of acetone, and the filtrate and the acetone wash are combined and evaporated under reduced pressure to remove most of the acetone. The residue is partitioned between methylene chloride and water. The methylene chloride layer is separated and washed with 5% aqueous sodium thiosulfate then with water. The methylene chloride solution is dried over sodium sulfate and evaporated under reduced pressure to give about 33.47 g. of a residue comprising 1-iodo-cis,cis-6,9,12-octadecatriene.

The infrared spectrum in mineral oil shows $\nu_{max}$. 3010, 1680, 1650, 720 cm$^{-1}$.

Calcd for C$_{10}$H$_{31}$I: C, 57.76; H, 8.29: I, 33.95 Found: C, 58.30; H, 8.71; I, 32.62

NMR Spectrum in CCl$_4$ shows peaks centered at 5.4 δ (vinyl H), 3.18 δ (CH$_2$-I protone),

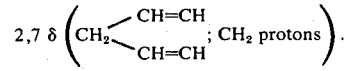

C. 2-Methyl-cis,cis,cis-8,11,14-elcosatrienoic acid

A solution of 28 g. of sodium in 200 ml. of freshly distilled n-butanol is prepared by adding the sodium in small pieces and stirring under a nitrogen atmosphere until all the sodium is dissolved, then 17.1 ml. of diethyl methylmalonate is added and the solution is heated under reflux for 1 hr. The solution is then cooled and a solution of 33.47 g. of 1-iodo-cis,cis-6,9,12-octadecatriene in 100 ml. of freshly distilled n-butanol is added. The thus obtained reaction mixture is stirred and heated under reflux in a nitrogen atmosphere for 3 hrs., then the n-butanol is removed by evaporation under reduced pressure. The residue is partitioned between methylene chloride and 2N hydrochloric acid. The methylene chloride solution is separated and washed with aqueous sodium bicarbonate, then with water until the washings are neutral, and dried over sodium sulfate. The solvent is removed by evaporation under reduced pressure to give a residue of crude diethyl ester. The residue is dissolved in 50 ml. of 3A alcohol and added to a solution of 25 g. of potassium hydroxide in 500 ml. of 3A alcohol. The mixture is stirred and heated under reflux in a nitrogen atmosphere for 3 hrs., than 10 ml. of water is added and stirring is continued for an additional hour. The ethanol is then removed by evaporation under reduced pressure, and 500 ml. of ether and 100 ml. of water are added to the residual mixture. The aqueous and the ether layers are separated and the ether layer is twice extracted with 5% aqueous sodium hydroxide. The three aqueous extracts are combined and made acid with 2N hydrochloric acid. The acidified mixture is extracted three times with ethyl acetate. The ethyl acetate extracts are washed with water until the washes are neutral, and the water washes are back extracted with ethyl acetate. The ethyl acetate extracts are combined, dried over magnesium sulfate, and evaporated under reduced pressure to give a residue of crude dicarboxylic acid. The thus obtained residue is dissolved in 185 ml. of quinoline and stirred and heated slowly, in a nitrogen atmosphere, to 120°C. When the temperature reaches 70°C., 5.0 g. of copper powder is added in small portions. The temperature is maintained at 120°C. for 2 hrs., then the mixture is cooled and poured into excess ice and hydrochloric acid; the mixture should stay acidic. The mixture is extracted 3 times with 500 ml. portions of methylene chloride. The methylene chloride extracts are combined and washed twice with 2N hydrochloric acid, then with water until the washings are neutral, and dried over sodium sulfate. The dried solution is evaporated under reduced pressure to give a residue comprising 2-methyl-cis,cis,cis-8,11,14-eicosatrienoic acid.

The NMR spectrum is in agreement with the assigned structure (6 vinyl protons centered at 5.4 δ; 4 doubly allylic protons centered at 2.7δ). The material is homogeneous by thin layer chromatography.

Preparation 4

11,15-Dimethyl-8,11,14-eicosatrienoic acid

A. Methyl 4-methyl-3-nonenoate

A mixture of 5 g. of 1-bromo-3-methyl-2-octane (from Preparation 2, part C), 7 g. of potassium cyanide and 35 ml. of dimethylsulfoxide is stirred and heated under nitrogen for 2.5 hrs. at about 110°C. The mixture is then poured into water and extracted with ether. The ether extract is washed with water, then with saturated aqueous sodium chloride, dried over sodium sulfate, and evaporated under reduced pressure leavng a residue comprising 4-methyl-3-nonenonitrile. The thus obtained residue is mixed with 45 ml. of 25% hydrogen chloride in methanol containing 0.5 ml. of water while cooling with an ice bath, then the ice is allowed to melt and the mixture is stirred for about 18 hours. The mixture is poured into water and extracted with ether. The ether extract is washed with water, aqueous sodium bicarbonate, saturated aqueous sodium chloride, dried over sodium sulfate, and evaporated under reduced pressure leaving a residue comprising methyl 4-methyl-3-nonenoate. The thus obtained residue is dissolved in a mixture of 30 ml. of 95% ethanol, 2.5 g. of potassium hydroxide, and 3.0 ml. of water and heated under reflux under nitrogen for about 2 hours, then water and Skellysolve "B" (mixed hexanes) are added. The aqueous and organic layers are separated and the aqueous layer is made acid wit 3N hydrochloric acid, then extracted with ether. The extract is dried over sodium sulfate and evaporated under reduced pressure to give a residue comprising 4-methyl-3-nonenoic acid.

A solution of 10 g. of 4-methyl-3-nonenoic acid in 200 ml. of methanol containing 2 g. of hydrogen chloride is stirred and heated under reflux, under nitrogen, for about 6 hrs., then is allowed to stand about 18 hrs. at room temperature. The mixture is then concentrated under reduced pressure until most of the methanol is removed, poured into ice water, and extracted with ether. The ether extracts are washed with water, then with saturated aqueous sodium bicarbonate, and saturated aqueous sodium chloride. The ether solution is then dried over sodium sulfate and evaporated to give a residue comprising methyl 4-methyl-3-nonenoate.

B. 1-Bromo-4-methyl-3-nonene

A solution of 2.5 g. of lithium aluminum hydride in 150 ml. of anhydrous ether is prepared and a solution of 5.0 g. of methyl 4-methyl-3-nonenoate in 50 ml. of anhydrous ether is added dropwise, with stirring, under nitrogen. The reaction mixture is then heated under reflux for about 6 hrs., then cooled, and 30 ml. of ethyl acetate is slowly added. Water is added until the inorganic salts separate, then 2 g. of Celite (diatomaceous earth filter aid) is added and the mixture is filtered through sodium sulfate. The filtrate is dried over sodium sulfate and evaporated under reduced pressure to give a residue comprising 4-methyl-3-nonen-1-ol.

A solution of 3 g. of 4-methyl-3-nonen-1-ol in a mixture of 20 ml. of ether and 1.25 ml. of pyridine under nitrogen is cooled in an ice-salt bath and stirred while 2.7 ml. of phosphorus tribromide is added slowly. The ice bath is removed and the mixture is allowed to warm to room temperature, then is heated under reflux for about 2.5 hrs. The mixture is then cooled in an ice bath while 10 ml. of water is added slowly. The layers are separated and the ether layer is washed with water, saturated aqueous sodium bicarbonate, saturated aqueous sodium chloride, dried over sodium sulfate, and evaporated, giving a residue comprising 1-bromo-4-methyl-3-nonene.

C. Methyl 2,6-dimethyl-2,5-undecadienoate

A mixture of 5.0 g. of 1-bromo-4-metyl-3-nonene and 6.35 g. of triphenylphosphine in 25 ml. of dry benzene is heated under reflux for 12 hrs., then the mixture is allowed to cool to 25°C. and 50 ml. of dry ether and 11 ml. of 15% n-butyl lithium in hexane are added. The resulting mixture is stirred for 2 hrs. at 25°C., giving a red solution, then 2.5 g. (2.15 ml.) of methyl pyruvate in 10 ml. of ether is added and the mixture is stirred at room temperature (about 25°C.) for 18 hrs. The solvents are then removed by evaporation under reduced pressure and the resulting residue is dissolved in methylene chloride and chromatographed over silica gel. Elution with 5,10 and 20% ethyl acetate in cyclohexane and evaporation of the eluate fractions gives a residue comprising methyl 2,6-dimethyl-2,5-undecadienoate.

D. 1-Bromo-2,6-dimethyl-2,5-undecadiene

Following the procedure of part B of this preparation but replacing methyl 4-methyl-3-nonenoate as starting material with a stoichiometrically equivalent amount of methyl 2,6-dimethyl-2,5-undecenoate there is obtained 1-bromo-2,6-dimethyl-2,5-undecadiene.

E. 1-Chloro-10,14-dimethylnonadeca-10,13-dien-7-yne

A solution of 12.0 g. of 1-chlorooct-7-yne in 20 ml. of tetrahydrofuran is added to a mixture of 27 ml. of 3N ethyl magnesium bromide in ether and 50 ml. of tetrahydrofuran. The mixture is stirred and heated under reflux for 30 min. under nitrogen, then 0.45 g. of powdered cuprous chloride is added and heating and stirring is continued for 20 min. A solution of 20.0 g. of 1-bromo-2,6-dimethyl-2,5-undecadiene in 15-ml. of tetrahydrofuran is added and the mixture is heated under reflux for 10 hrs., then allowed to stand for about 18 hrs., and poured into saturated aqueous ammonium chloride and ether. The mixture is filtered and the ether solution is separated, washed with water, dried over sodium sulfate, and evaporated to leave a residue comprising 1-chloro-10,14-dimethylnonadeca-10,13-dien-7-yne.

F. 1-Chloro-10,14-dimethylnonadeca-7,10,13-triene

A mixture of 5.0 g. of 1-chloro-10,14-dimethylnonadeca-10,13-dien-7-yne 500 mg. of 5% palladium-barium sulfate catalyst and 40 ml. of pyridine is shaken under hydrogen for about 2 hrs. (until the uptake of hydrogen practically ceases). The mixture is then filtered, diluted with water, and extracted with ether. The ether extract is washed with water, dilute hydrochloric acid, and aqueous sodium bicarbonate, then is dried over sodium sulfate and evaporated to leave a residue comprising 1-chloro-10,14-dimethylnonadeca-7,10,13-triene.

G. 11,15-Dimethyl-8,11,14-eicosatrienoic acid

A mixture of 10.0 g. of 1-chloro-10,14-dimethyl-nonadeca-7,10,13-triene, 10 g. of potassium cyanide and 50 ml. of dimethyl-sulfoxide is heated under nitrogen at 115° with stirring for about 2.5 hrs., then is allowed to cool, poured into water, and extracted with ether. The ether extract is washed with water, dried over sodium sulfate, and evaporated. The residue is stirred with 90 ml. of 25% hydrogen chloride in methanol while cooling with ice. The ice is allowed to melt and stirring is continued for a total time of about 20 hrs., then water is added and the mixture is extracted with ether. The ether extract is washed with water, dried over sodium sulfate, and evaporated. The residue is distilled in a rocking short-path distillation apparatus at about 0.005 mm. to give a distillate comprising methyl 11,15-dimethyl-8,11,14-eicosatrienoate. The thus obtained methyl ester is dissolved in a mixture of 75 ml. of 95% ethanol and 6.0 g. of potassium hydroxide in 6 ml. of water, and the mixture is heated under reflux for 2 hours, then 150 ml. of water is added and 150 ml. of ether. The water layer is separated, made acid with 3N hydrochloric acid, and extracted with ether. The ether extracts are washed with water, dried over sodium sulfate and evaporated to give a residue comprising 11,15-dimethyl-8,11,14-eicosatrienoic acid, which can be further purified by distillation in a short-path tube at a pressure of about 0.005 mm.

Preparation 5

8,12-Dimethyl-8,11,14-eicosatrienoic acid

A. 3-Nonenoic acid

A mixture of 5 g. of 1-bromo-2-octyne, 7 g. of potassium cyanide and 35 ml. of dimethylsulfoxide is stirred and heated under nitrogen for about 2.5 hrs. at reflux temperature. The mixture is then poured into water and extracted with ether. The ether extract is washed with water, than with saturated aqueous sodium chloride, dried over sodium sulfate, and evaporated under reduced pressure leaving a residue comprising 3-nonynenitrile. The thus obtained residue is mixed with 45 ml. of 25% hydrogen chloride in methanol containing 0.5 ml. of water while cooling in an ice bath. The ice is allowed to melt and the mixture is stirred for about 18 hrs., then is poured into water and extracted with ether. The ether extract is washed with water, aqueous sodium bicarbonate, and saturated aqueous sodium chloride, dried over sulfate, and evaporated under reduced pressure leaving a residue comprising methyl 3-nonynoate. A mixture of the thus obtained methyl 3-nonynoate, 500 mg. of 5% palladium-barium sulfate catalyst and 40 ml. of pyridine is shaken under hydrogen for about 2 hrs., until the uptake of hydrogen practically ceases. The mixture is then filtered, diluted with water, and extracted with ether. The ether extract is washed with water, dilute hydrochloric acid, and aqueous sodium bicarbonate, then is dried over sodium sulfate and evaporated to leave a residue comprising methyl 3-nonenoate.

The residue of methyl 3-nonenoate is dissolved in a mixture of 30 ml. of 95% ethanol, 2.5 g. of potassium hydroxide, and 3 ml. of water and heated under reflux under nitrogen for about 2 hrs., then water and Skellysolve "B" (mixed hexanes) are added. The aqueous layer is separated and made acid with 3N hydrochloric acid, then extracted with ether. The ether extract is dried over sodium sulfate and dried under reduced presure to give a residue comprising 3-nonenoic acid.

B. 4-Decen-2-one

A mixture of 22 g. of 3-nonenoic acid and 100 ml. of thionyl chloride is stirred at room temperature for about an hour, then 150 ml. of 1:1 ether-benzene mixture is added. The solvents are removed by evaporation under reduced pressure, then another 150 ml. of 1:1 ether benzene mixture is added to the residue, and removed by evaporation under reduced pressure, leaving a residue comprising 3-nonenoyl chloride. This residue is then dissolved in 30 ml. of benzene.

A mixture of 68 ml. of 3M methyl magnesium bromide in ether and 70 ml. of ether is cooled in an ice bath while 18.3 g. of dry cadmium chloride is added in portions. The ice bath is removed and the mixture is heated under reflux for about 45 minutes, then most of the ether is removed by evaporation under reduced pressure and 70 ml. of benzene is added, followed by slow addition of the 3-nonenoyl chloride in benzene solution prepared above. The thick, white mixture is heated under reflux for one hour, then is cooled in an ice bath and 60 ml. of ice water is added, followed by enough 1N sulfuric acid to give two clear phases. The organic layer is separated and washed with water, saturated aqueous sodium bicarbonate, dried, and distilled through a Vigreaux column to give a distillate comprising 4-decen-2-one.

C. 3-Hydroxy-3-methylundec-5-en-1-yne

A mixture of 45.5 g. of lithium acetylide-ethylene diamine, 200 ml. of dry tetrahydrofuran, and 200 ml. benzene at 35°C. is stirred under nitrogen while 50 g. of 4-decen-2-one in 50 ml. of benzene is added slowly. The mixture is then stirred for about 2.5 hrs., and 130 ml. of water is added slowly. The mixture is heated under reflux for one hour, cooled, and extracted with ether. The ether extract is washed with water, 1N hydrochloric acid, saturated aqueous sodium bicarbonate, and saturated aqueous sodium chloride, then is dried and evaporated under reduced pressure. The residue is distilled through a Vigreaux column giving a distillate comprising 3-hydroxy-3-methylundec-5-en-1-yne.

D. 3-Hydroxy-3-methyl-1,5-undecadiene

A mixture of 20.0 g. of 3-hydroxy-3-methyl-undec-1-yne, 200 ml. of pyridine, and 500 mg. of 5% palladium on barium sulfate is shaken in hydrogen at an initial pressure of 45 lb./sq. in. The hydrogenation is stopped when the calculated amount for one mole uptake per mole of compound has been absorbed. The mixture is poured into water and extracted with ether. The ether extract is washed with water, dilute hydrochloric acid, aqueous sodium bicarbonate, dried, and evaporated under reduced pressure to give a residue which is distilled through a Vigreaux column to give a distillate comprising 3-hydroxy-3-methyl-1,5-undecadiene.

E. 1-Bromo-3-methyl-2,5-undecadiene

In an ice-salt bath 25 ml. of 48% hydrobromic acid is saturated with hydrogen bromide by bubbling through for 5 to 10 min., then 10 g. of 3-hydroxy-3-methylundec-1-ene is added slowly, with stirring. After an additional 20 min. of stirring benzene is added, then the benzene layer is separated, washed with icewater, saturated aqueous sodium bicarbonate, saturated sodium chloride, dried, and evaporated under reduced pressure giving a residue which is distilled through a Vigreaux column to give a main fraction of distillate comprising 1-bromo-3-methyl-2,5-undecadiene.

F. 1-Bromo-4-methyl-3,6-dodecadiene

Following the procedure of Preparation 4, part A, but replacing 1-bromo-3-methyl-2-octene as starting material with 1-bromo-3-methyl-2,5-undecadiene is productive of methyl 4-methyl-3,6-dodecadienoate.

Following the procedure of Preparation 4, part B, but replacing methyl 4-methyl-3-nonenoate as starting material with methyl 4-methyl-3,6-dodecadienoate is productive of 1-bromo-4-methyl-3,6-dodecadiene.

G. Methyl 2,6-dimethyl-2,5,8-tetradecatrienoate

Following the procedure of Preparation 4, part C, but replacing 1-bromo-4-methyl-3-nonene as starting material with a stoichiometrically equivalent amount of 1-bromo-4-methyl-3,6-dodecadiene is productive of methyl 2,6-dimethyl-2,5,8-tetradecatrienoate.

H. 1-Bromo-2,6-dimethyl-2,5,8-tetradecatriene

Following the procedure of Preparation 4, part B, but replacing methyl 4-methyl-3-nonenoate as starting material with a stoichiometrically equivalent amount of methyl 2,6-dimethyl-2,5,8-tetradecatrienoate is productive of 1-bromo-2,6-dimethyl-2,5,8-tetradecatriene.

I. 8,12-Dimethyl-8,11,14-eicosatrienoic acid

A solution of 22 g. of 1-bromo-2,6-dimethyl-2,5,8-tetradecatriene, and 20 g. of methyl 6-iodohexanoate in 60 ml. of a 1:1 mixture of anhydrous ether and benzene is added to 2.5 g. of magnesium in 30 ml. of ether over a period of 5 min., a crystal of iodine and 20 mg. of mercuric chloride are introduced, and the mixture is heated under reflux under nitrogen for about 3 hr., then an additional 20 mg. of mercuric chloride is introduced and heating is continued for a further 3 hrs. The reaction mixture is then cooled to 5°–10°C. and treated with dilute hydrochloric acid. The upper layer is then separated and the organic layer is extracted with ether. The extracts are combined and washed with aqueous sodium bisulfite, saturated aqueous sodium bicarbonate and dried over sodium sulfate, then evaporated under reduced pressure to give a residue. The residue is distilled at a pressure of about 0.1 mm. After collecting some unchanged starting material a distillate fraction comprising methyl 8,12-dimethyl-8,11,14-eicosatrienoate is collected.

A solution of 5 g. of the thus obtained methyl ester in a mixture of 75 ml. of 95% ethanol and 5.0 g. of potassium hydroxide in 5 ml. of water is heated under reflux under nitrogen for about 2 hrs., then 150 ml. of water and 150 ml. of ether are added. The water layer is separated and made acid with 3N hydrochloric acid, and extracted with ether. The ether extracts are washed with water, dried over sodium sulfate, and evaporated to give a residue comprising 8,12-dimethyl-8,11,14-eicosatrienoic acid.

Preparation 6

3-Methyl-8,11,14-eicosatrienoic acid

A. Cis,cis,cis-6,9,12-octadecatrienol

A solution of 50 g. of methyl γ-linolenate in 400 ml. of absolute ether is added dropwise with stirring to a suspension of 250 g. of lithium aluminum hydride in 1400 ml. of ether under nitrogen. Stirring is continued on the mixture is heated under reflux for 6 hrs. The mixture is then cooled in an ice bath and stirred while 300 ml. of ethyl acetate is added dropwise, followed by addition of water until the inorganic salts separate. Next, 20 g. of Celite (diatomaceous earth filter aid) is added and the mixture is filtered. The filtrate is dried over sodium sulfate and evaporated under reduced pressure to give 47.26 g. of a residue comprising cis,cis,cis-6,9,12-octadecatrienol.

B. Cis,cis,cis-6,9,12-octadecatrienal

A solution of 20 g. of cis,cis,cis-6,9,12-octadecatrienol in 400 ml. of acetone is cooled to −10°C. and 40 ml. of Jones reagent (10.3 g $CrO_3$, 30 ml. $H_2O$, 8.7 ml. concentrated $H_2SO_4$) is added dropwise over a period of 10 min. while stirring. The reaction mixture is stirred for an additional 15 min. at −10°C. then the excess Jones reagent is destroyed by addition of 25 ml. of isopropanol. The reaction mixture is diluted with water and extracted several times with ether. The ether extracts are combined and washed with aqueous sodium bicarbonate, then water, and dried over sodium sulfate, then evaporated under reduced pressure to give a residue comprising cis,cis,cis-6,9,12-octadecatrienal.

C. Cis,cis,cis-7,10,13-nonadecatrien-2-ol

A solution of 26 g. of cis,cis,cis-6,9,12-octadecatrienal in 200 ml. of absolute ether is added slowly with stirring, to a solution of 0.15 moles of methyl magnesium bromide in 200 ml. of ether (50 ml. of 3N methyl magnesium bromide in ether diluted with absolute ether to 200 ml.) while heating under reflux under nitrogen. Heating is continued for an hour after addition of the aldehyde is completed, then the reaction mixture is cooled in an ice bath and 200 ml. of 1N hydrochloric acid is added with caution. The ether layer is separated, washed with aqueous sodium bicarbonate, dried over sodium sulfate, and evaporated under reduced pressure to give a residue comprising cis,cis,cis-7,10,13-nonadecatrien-2-ol.

D. 2-iodo-cis,cis,cis-7,10,13-nonadecatriene

A solution of 28 g. of cis,cis,cis-7,10,13-nonadecatrien-2-ol in 300 ml. of pyridine is cooled in an ice-salt bath and stirred while a solution of 45.0 g. of p-toluenesulfonyl chloride in 100 ml. of pyridine is added over a period of 30 min., then the ice-salt bath is removed and the reaction is allowed to proceed for 3 hrs. at room temperature. The reaction mixture is then poured into 1000 ml. of ice and water, and hydrochloric acid is added carefully until the mixture is acidic. The mixture is extracted with 4 200-ml. portions of methylene chloride, adding ice if needed to keep the temperature at 0°C. The methylene chloride solutions are combined and washed with ice cold 5% aqueous hydrochloric acid, then with cold saturated aqueous sodium bicarbonate, and finally with water until the washings are neutral. The methylene chloride solution is then dried over sodium sulfate, and evaporated under reduced pressure to give a residue comprising cis,cis,-cis-7,10,13-nonadecatrien-2-ol p-toluenesulfonate. The thus obtained p-toluenesulfonate is dissolved in 5000 ml. of acetone, 60 g. of powdered sodium iodide is added, and the mixture is stirred and heated under reflux, under nitrogen, for 4 hours. Next the mixture is cooled and filtered to remove precipitated sodium p-toluenesulfonate. The filtrate is evaporated under reduced pressure and the thus obtained residue is dissolved in methylene chloride and water. The methylene chloride solution is separated and washed with water, then with aqueous 5% sodium thiosulfate, again with water, then is dried over sodium sulfate and evaporated under reduced pressure to give a residue comprising 2-iodo-cis,cis,cis-7,10,13-nonadecatriene.

E. 3-Methyl-8,11,14-eicosatrienoic acid

A solution of sodium butoxide is prepared by adding 2.8 g. of metallic sodium in small pieces to 200 ml. of freshly distilled n-butanol under nitrogen while stirring, then 15.3 ml. of diethyl malonate is added and the mixture is heaed under reflux for 1 hour. The mixture is cooled, and a solution of 34 g. of 2-iodo-cis,cis,cis-7,10,13-nonadecatriene in 200 ml. of freshly distilled n-butanol is added. The resulting reaction mixture is heated under reflux under nitrogen with stirring for 3 hrs., then the n-butanol is removed by distillation under reduced pressure. The thus obtained residue is partitioned between methylene chloride and 2N hydrochloric aid. The methylene chloride solution is separated, washed with aqueous sodium bicarbonate, then with water until the washings are neutral, dried over sodium sulfate, and evaporated under reduced pressure to give a residue. The residue is dissolved in 50 ml. of 95% alcohol and added to a solution of 25 g. of potassium hydroxide in 500 ml. of 95% ethanol, then is stirred and heated under reflux, under nitrogen, for 3 hrs., at which time 10 ml. of water is added and heating is continued for one more hour. The ethanol is then removed by distillation under reduced pressure and 500 ml. of ether and 100 ml. of water are added. The aqueous layer is separated and the ether is extracted with 5% aqueous sodium hydroxide. The aqueous layers are combined and made acid with 2N hydrochloric acid, then are extracted three times with ethyl acetate. The ethyl acetate extracts are combined and washed with water until the washes are neutral, dried over magnesium sulfate and evaporated under reduced pressure to give a residue. The residue is dissolved in 200 ml. of quinoline and stirred and heated under nitrogen. The mixture is slowly heated (30 min.) to 120°C. When the temperature reaches 70°C. 5 g. of copper powder is added in small portions. The temperature is maintained at 120°C. for 2 hrs., then the mixture is cooled and poured into excess ice and hydrochloric acid. The mixture should stay acidic. The mixture is extracted with 3 500-ml. portions of methylene chloride. The extracts are combined and washed twice with 3N hydrochloric acid, then with water until the aqueous washings are neutral, dried over sodium sulfate, and evaporated under reduced pressure to give a residue comprising 3-methyl-cis,cis,cis-8,11,14-eicosatrienoic acid.

Example 1

Racemic 7-[3α,5α-peroxy-2β-(2-octenyl)cyclopent-1α-yl]heptanoic acid (9,11-peroxy-14-prostenoic acid) (2) and racemic 7-[3α,5α-peroxy-2β-(3-hydroperoxy-1-octenyl)cyclopent-1α-yl]heptanoic acid (9,11-peroxy-15-hydroperoxy-13-prostenoic acid) (3).

A solution of 1.0 g. of bishomo-γ-linolenic acid (cis, cis, cis-8,11-14-eicosatrienoic acid) in 4.5 ml. of 1N aqueous sodium hydroxide is diluted to 100 ml. with water, then 40 mg. of hematoporphyrin hydrochloride and 25 mg. of 2,6-di-t-butyl-p-cresol are added and the mixture is stirred in an atmosphere of oxygen while irradiating with external "daylight" fluorescent tubes placed close to the glass reaction vessel. After about 40 hr. an additional 40 mg. of hematoporphyrin hydrochloride is added to replace that which has been bleached. After a total of about 75 hrs. of stirring and irradiation about 160 ml. of oxygen has been absorbed. The solution is then acidified with dilute hydrochloric acid and extracted with ether. The ether solution is separated and washed with water, then with saturated aqueous sodium chloride. The washed ether solution is then dried over anhydrous sodium sulfate, filtered, and evaporated to leave a nearly colorless oil, comprising a mixture of racemic 7-[3α,5α-peroxy-2β-(2-octenyl)-cyclopent-1α-yl]heptanoic acid (2) racemic 7-[3α,5α-peroxy-2β-(3-hydroperoxy-1-octenyl)cyclopent-1α-yl]heptanoic acid (3), and bishomo-γ-linolenic acid (1). The thus obtained mixture is dissolved in a small amount of ethyl acetate and chromatographed on 100 g. of acid-washed silica gel, eluting with ethyl acetate followed by ethyl acetate containing increasing percentages of methanol. Unchanged bishomo-γ-linolenic acid is eluted first, followed by racemic 7-[3α,5α-peroxy-2β-(2-octenyl)cyclopent-1α-yl]-heptanoic acid (2) and racemic 7-[3α,5α-peroxy-2β-(3-hydroperoxy-1-octenyl)cyclopent-1α-yl]heptanoic acid (3). The racemic 7-[3α,5α-peroxy-2β(2-octenyl)-cyclopent-1α-yl]heptanoic acid (2) and racemic 7-[3α,5α-peroxy-2β-(3-hydroperoxy-1-octenyl)-cyclopent-1α-yl]heptanoic acid (3) obtained by evaporation of the chromatogram eluates can each be used without further purification or can be further purified by reversed phase partition chromatography or countercurrent distribution.

Example 2

Racemic 7-[3α,5α-peroxy-2β-(2-octenyl)cyclopent-1α-yl]heptanoic acid (2) and racemic 7-[3α,5α-peroxy-2β-(3-hydroperoxy-1-octenyl)-cyclopent-1α-yl]heptanoic acid (3).

A solution of 3.06 g. (10 mmoles) of bishomo-γ-linolenic acid (1) in 50 ml. of benzene is stirred with 7.25 g. (20 mmoles) of the endoperoxide of 9,10-diphenylanthracene and the mixture is slowly warmed until the endoperoxide begins to decompose and liberate singlet oxygen. Stirring is continued at this temperature until decomposition of the anthracene endoperoxide is complete. The mixture is then concentrated to a small volume and chromatographed on 300 g. of acid washed silica gel. The chromatogram column is eluted first with 1:1 benzene-ethyl acetate, then ethyl acetate, and finally 5–15% methanol in ethyl acetate, and the eluate fractions are evaporated to give first 9,10-diphenyl anthracene, followed by bishomo-γ-linolenic acid (1), racemic 7-[3α,5α-peroxy-2β-(2-octenyl)-cyclopent-1α-yl]heptanoic acid (2) and racemic 7[3α,5α-peroxy-2β-(3-hydroperoxy-1-octenyl)cyclopent-1α-yl]heptanoic acid (3). The products are sufficiently pure for further use, or can be further purified as described above.

Example 3

Racemic
7-3α,5α-peroxy-2β-(2-octenyl)cyclopent-1α-yl]heptanoic acid (2) and racemic
7-[3α,5α-peroxy-2β-(3-hydroperoxy-1-octenyl)-cyclopent-1α-yl]heptanoic acid (3).

The adduct of ozone and tri-(p-tolyl)phosphite (25 mmoles) in methylene chloride at −70° C. is prepared as described by Q. E. Thompson, J. Am. Chem. Soc. 83, 845 (1961). To this cold solution is added a solution of 3.06 g. (10 mmoles) of bishomo-y-linolenic acid in 25 ml. of cold methylene chloride. The solution is then stirred and allowed to warm slowly to room temperature, after which stirring is continued for about 30 minutes, then the solution is concentrated to a small volume and chromatographed on 300 g. of acid-washed silica gel. Elution with a 1:1 mixture of benzene-ethyl acetate followed by ethyl acetate and finally 5–15% methanol in ethyl acetate and evaporation of the eluates gives residues comprising bishomo-y-linolenic acid (1), racemic 7-[3α,5α-peroxy-2β-(2-octenyl)-cyclopent-1α-yl]heptanoic acid (2) and racemic 7-[3α,5α-peroxy-2β-(3-hydroperoxy-1-octenyl)cyclopent-1α-yl]heptanoic acid (3). The thus-obtained products are sufficiently pure for use in further transformations, or can be further purified as described above.

Example 4

Racemic
7-[3α,5α-peroxy-2β-(2-octenyl)cyclopent-1α-yl]heptanoic acid (2) and racemic 7-[3α,5α-peroxy-2β-(3 -hydroperoxy-1-octenyl)cyclopent-1α-yl]heptanoic acid (3).

The effluent gases resulting from the electrodeless discharge of radio frequency current through oxygen in an apparatus as described by E. J. Corey, J. Am. Chem. Soc., 86, 3881 (1964), are bubbled through a solution of 300 mg. of bishomo-γ-linolenic acid in 25 ml. of chlorobenzene at 25° containing 50 mg. of 2,6-di-t-butyl-p-cresol for a period of about 48 hrs. The solution is then concentrated under diminished pressure, and the thus obtained residue is dissolved in a small amount of ethyl acetate and chromatographed over 50 g. of acid washed silica gel. On elution with ethyl acetate containing increasing amounts of methanol and evaporation of the eluates there is obtained first racemic 7-[3α,5α-peroxy-2β-(2-octenyl)cyclopent-1β-yl]heptanoic acid (2) and then racemic 7-[3α,5α-peroxy-2β-(3-hydroperoxy-1-octenyl)-cyclopent-1β-yl]heptanoic acid (3). The products which are sufficiently pure for use in subsequent transformations, can be further purified as described above.

Example 5

Racemic
7-[3α,5α-peroxy-2β-(2-octenyl)cyclopent-1α-yl]heptanoic acid (2) and racemic
7-[3α,5α-peroxy-2β-(3-hydroperoxy-1-octenyl)cyclopent-1α-yl]heptanoic acid (3).

A solution of 3.06 g. of bishomo-γ-linolenic acid in 300 ml. of methanol is cooled to 10°C. and stirred, then 19.2 ml. of 30% hydrogen peroxide is added, followed by 145 ml. of 103M sodium hypochlorite added over a period of 90 minutes. The solution is then diluted with water, made acid by addition of dilute aqueous hydrochloric acid, and extracted with ether. The ether layer is separated, washed with water then with saturated aqueous sodium chloride, dried over sodium sulfate, and evaporated to give a residue comprising racemic 7-[3α,5α-peroxy-2β-(2-octenyl)cyclopent-1α-yl]heptanoic acid (2) and racemic 7-[3α,5α-peroxy-2β-(3-hydroperoxy-1-octenyl)cyclopent-1α-yl]-heptanoic acid (3). The thus obtained residue is chromatographed over 300 g. of acid washed silica gel following the procedure of Example 1 to give racemic 7-[3α,5α-peroxy-2β-(2-octenyl)cyclopent-1α-yl]heptanoic acid (2) and racemic 7-[3α,5α-peroxy-2β-(3-hydroperoxy-1-octenyl)cyclopent-1α-yl]heptanoic acid (3) which can each be used directly for subsequent transformations or can be further purified as described above.

Example 6

Racemic
7-[3α,5α-peroxy-2β-(2-octenyl)-cyclopent-1α-yl]heptanoic acid (2) and racemic
7-[3α,5α-peroxy-2β-(3α-hydroperoxy-1-octenyl)cyclopent-1α-yl]heptanoic acid (3).

A solution of 3.06 g. of bishomo-γ-linolenic acid in 25 ml. of ethanol containing 2 g. of potassium hydroxide and 5 ml. of benzyl cyanide is treated dropwise with 5 ml. of 30% hydrogen peroxide at room temperature. When the oxygen evolution has ended the solution is diluted with water, made acid with dilute aqueous hydrochloric acid, and concentrated under diminished pressure until the ethanol is removed. The aqueous residue is then extracted with ether and the ether extract is washed with water, then with saturated aqueous sodium chloride, dried over sodium sulfate, and evaporated under reduced pressure to give a residue comprising racemic 7-[3α,5α-peroxy-2β-(2-octenyl)cyclopent-1α-yl]heptanoic acid (2) and racemic 7-[3α,5α-peroxy-2β-(3-hydroperoxy-1-octenyl)cyclopent-1α-yl]heptanoic acid (3). The products can be separated by chromatography over 300 g. of acid washed with silica gel following the procedure of Example 1.

Example 7

Racemic
8-[3α,5α-peroxy-2β-(2-octenyl)-cyclopent-1α-yl]octanoic acid (2) and racemic
8-[3α,5α-peroxy-2β-(3-hydroperoxy-1-octenyl)cyclopent-1α-yl]octanoic acid (3).

Following the procedure of Examples 1 to 6, but substituting as starting material cis,cis,cis-9,12,15-heneicosatrienoic acid in place of bishomo-γ-linolenic acid is productive of racemic 8-[3α,5α-peroxy-2β-(2-octenyl)cyclopent-1α-yl]octanoic acid (2) and racemic 8-[3α,5α-peroxy-2β-(3-hydroperoxy-1-octenyl)- cyclopent-1α-yl]octanoic acid (3), which can be isolated and purified as described in the above Examples.

Following the procedure of Examples 1 to 6, but substituting for bishomo-γ-linolenic acid as starting material the following acids:
7,10,13-hexadecatrienoic acid,
6,9,12-octadecatrienoic acid,
9,12,15-octadecatrienoic acid (linolenic acid),
7,10,13-nonadecatrienoic acid,
4,7,10,13-nonadecatetraenoic acid,
5,8,11-eicosatrienoic acid,
5,8,11,14-eicosatetraenoic acid (arachidonic acid),
8,11,14,17-eicosatetraenoic acid,
7,10,13-docosatrienoic acid,
7,10,13,16-docosatetraenoic acid,
15-methyl-8,11,14-eicosatrienoic acid,
16-methyl-8,11,14-eicosatrienoic acid,
11,15-dimethyl-8,11,14-eicosatrienoic acid,
8,12-dimethyl-8,11,14-eicosatrienoic acid, and 16,16-dimethyl-8,11,14-eicosatrienoic acid,
there are obtained:

racemic 6-[3α,5α-peroxy-2β-(2-pentenyl)cyclopent-1α-yl]hexanoic acid (2) and racemic 6-[3α,5α-peroxy-2β-(3-hydroperoxy-1-pentenyl)cyclopent-1α-yl]hexanoic acid (3), racemic 5-[3α,5α-peroxy-2β-(2-octenyl)cyclopent-1α-yl]pentanoic acid (2) and racemic 5-[3α,5α-peroxy-2β-(3-hydroperoxy-1-octenyl)-cyclopent-1α-yl]pentanoic acid (3), racemic 8-[3α,5α-peroxy-2β-(2-pentenyl)cyclopent-1α-yl]-octanoic acid (2) and racemic 8-[3α,5α-peroxy-2β-(3-hydroperoxy-1-pentenyl)-cyclopent-1α-yl]octanoic acid (3), racemic 6-[3α,5α-peroxy-2β-(2-octenyl)cyclopent-1α-yl]-hexanoic acid (2) and racemic 6-[3α,5α-peroxy-2β-(3-hydroperoxy-1-octenyl)-cyclopent-1α-yl]-hexanoic acid (3), racemic 6-[3α,5α-peroxy-2β-(2-octenyl)cyclopent-1α-yl]-4-hexenoic acid (2) and racemic 6-[3α,5α-peroxy-2β-(3-hydroperoxy-1-octenyl)-cyclopent-1α-yl]-4-hexenoic acid (3), racemic 4-[3α,5α-peroxy-2β-(2-undecanyl)cyclopent-1α-yl]-butanoic acid (2) and racemic 4-[3α,5α-peroxy-2β-(3-hydroperoxy-1-undecanyl)-cyclopent-1α-yl]butanoic acid (3), racemic 7-[3α,5α-peroxy-2β-(2-octenyl)cyclopent-1α-yl]-5-heptenoic acid (2) and racemic 7-[3α,5α-peroxy-2β-(3-hydroperoxy-1-octenyl)-cyclopent-1α-yl]-5-heptenoic acid (3), racemic 10-[3α,5α-peroxy-2β-(2-pentenyl)cyclopent-1α-yl]-8-decanoic acid (2) and racemic 10-[3α,5α-peroxy-2β-(3-hydroperoxy-1-pentenyl)-cyclopent-1α-yl]-8-decanoic acid.

racemic 6-[3α,5α-peroxy-2β-(2-undecanyl)cyclopent-1α-yl]-hexanoic acid (2) and racemic 6-[3α,5α-peroxy-2β-(3-hydroperoxy-1-undecanyl)-cyclopent-1α-hexanoic acid (3).

racemic 9-[3α,5α-peroxy-2β-(2-octenyl)cyclopent-1α-yl]-7-nonenoic acid (2) and racemic 9-[3α,5α-peroxy-2β-(3-hydroperoxy-1-octenyl)-cyclopent-1α-yl]-7-nonenoic acid (3), racemic 7-[3α,5α-peroxy-2β-(3-methyl-2-octenyl)-cyclopent-1α-yl]heptanoic acid (2) and racemic 7-[3α,5α-peroxy-2β-(3-hydroperoxy-3-methyl-1-octenyl)cyclopent-1α-yl]heptanoic acid (3), racemic 7-[3α,5α-peroxy-2β-(2-octenyl)cyclopent-1α-yl]-heptanoic acid (2) and racemic 7-[3α,5α-peroxy-2β-(3-hydroperoxy-1-octenyl)-cyclopent-1α-yl]-heptanoic acid (3), racemic 7-[3α,5α-peroxy-3β-methyl-2β-(3-methyl-2-octenyl)-cyclo-pent-1α-yl]-heptanoic acid (2) and racemic 7-[3α,5α-peroxy-3β-methyl-2β-(3-hydroperoxy-3-methyl-1-octenyl)cyclopent-1α-yl]heptanoic acid (3), racemic 7-[3α,5α-peroxy-1β,2α-dimethyl-2β-(2-octenyl)-cyclopent-1α-yl]heptanoic acid (2) and racemic 7-[3α,5α-peroxy-1β,2α-dimethyl-2β-(3-hydroperoxy-1-octenyl)cyclopent-1α-yl]heptanoic acid (3), and racemic 7-[3α,5α-peroxy-2β-(4,4-dimethyl-2-octenyl)cyclopent-1α-yl]-heptanoic acid (2) and racemic 7-[3α,5α-peroxy-2β-(3-hydroperoxy-4,4-dimethyl-1-octenyl)-cyclopent-1α-yl]-heptanoic acid (3).

Example 8

Racemic 7-[3α,5α-peroxy-2β-(3-hydroperoxy-1-octenyl)cyclopent-1α-yl]heptanoic acid (3).

A solution of 2.0 g. of racemic 7-[3α,5α-peroxy-2β-(2-octenyl)cyclopent-1α-yl]heptanoic acid (2) in 9.0 ml. of 1N aqueous sodium hydroxide is diluted to 100 ml. with water, then 40 mg. of hematoporphyrin hydrochloride and 25 mg. of 2,6-dl-t-butyl-p-cresol are added and the mixture is stirred in an atmosphere of oxygen while irradiating with external "daylight" fluroescent tubes placed close to the glass reaction vessel. After about 40 hr. an additional 40 mg. of hematoporphyrin hydrochloride is added to replace that which has been bleached. After a total of about 75 hr. of stirring and irradiation the solution is acidified with dilute hydrochloric acid and extracted with ether. The ether solution is separated and washed with water, then with saturated aqueous sodium chloride, and dried over anhydrous sodium sulfate. The ether solution is then evaportated to give an oil which is dissolved in a small amount of ethyl acetate and chromatographed on 200 g. of acid washed silica gel. Elution with ethyl acetate containing increasing percentages of methanol and evaporation of the eluates gives racemic 7-[3α,5α-peroxy-2β-(3-hydroperoxy-1-octenyl) cyclopent-1α-yl]-heptanoic acid (3), which can be further purified by reversed phase partition chromatography or countercurrent distribution.

Following the procedure of Example 8, but substituting for racemic 7-[3α,5α-peroxy-2β-(2-octenyl)cyclopent-1α-yl]heptanoic acid (2) as starting material other acids of formula 2, for example racemic 8-[3α,5α-peroxy-2β-(2-octenyl)cyclopent-1α-yl] octanoate (2) and the other acids of formula 2 named following Example 7, is productive of the corresponding acids of formula 3, for example racemic 8-[3α,5α-peroxy-2β-(3-hydroperoxy-1-octenyl)cyclopent-1α-yl]octanoate (3) and the other acids of formula 3 named following Example 7.

Following the procedures of Examples 2 through 6, but substituting for bishomo-γ-linolenic acid as starting materal two equivalents of an acid of formula 2 is productive of the corresponding acid of formula 3, which can be isolated as shown above.

Example 9.

Racemic 7-[3α,5α-dihydroxy-2β-(3-hydroxy-1-octenyl)cyclopent-1α-yl]heptanoic acid (racemic prostaglandin F$_1$)(4).

To a solution of 1.0 g. of racemic 7-[3α,5α-peroxy-2β-(3-hydroperoxy-1-octenyl)cyclopent-1α-yl]heptanoate (3) in 25 ml. of isopropanol is added a solution of 1.0 g. of sodium borohydride in 5 ml. of 0.1N aqueous sodium hydroxide. The mixture is stirred for about an hour at room temperature, then is made acid with dilute hydrochloric acid and diluted with water. The mixture is then concentrated under reduced pressure until the isopropanol is removed, and the aqueous residue is extracted with ethyl acetate. The ethyl acetate extract is washed with water, then saturated aqueous sodium chloride, dried, and evaporated under reduced pressure. The residue is dissolved in a small amount of ethyl acetate and chromatographed over 100 g. of acid washed silica gel. The chromatogram is eluted with ethyl acetate containing increasing percentages of methanol and the eluate fractions are evaporated. The thus obtained residues are analyzed by thin layer chromatography (TLC), using silica gel or silver nitrate impregnated silica gel as adsorbent and developing with a mixture of 10 parts by volume of acetic acid, 10 parts of methanol, and 80 parts of chloroform. The residues showing an R$_f$ value of about 0.52 comprise racemic 7-[3α,5α-dihydroxy-2β-(3-hydroxy-1-octenyl)cyclopent-1α-yl]heptanoic acid.

Following the procedure of Example 9, but substituting for racemic 7-[3α,5α-peroxy-2β-(3-hydroperoxy-1-octenyl)cyclopent-1α-yl]heptanoic acid (3) as starting material other acids of formula (3), for example:

racemic 8-[3α,5α-peroxy-2β-(3-hydroperoxy-1-octenyl)-cyclopent-1α-yl]octanoic acid (3),
racemic 6-[3α,5α-peroxy-2β-(3-hydroperoxy-1-pentenyl)-cyclopent-1α-yl]hexanoic acid (3),
racemic 5-[3α,5α-peroxy-2β-(3-hydroperoxy-1-octenyl)-cyclopent-1α-yl]pentanoic acid,
racemic 8-[3α,5α-peroxy-2β-(3-hydroperoxy-1-pentenyl)-cyclopent-1α-yl]octanoic acid (3),
racemic 6-[3α,5α-peroxy-2β-(3-hydroperoxy-1-octenyl)-cyclopent-1α-yl]hexanoic acid (3),
racemic 6-[3α,5α-peroxy-2β-(3-hydroperoxy-1-octenyl)-cyclopent-1α-yl]-4-hexanoic acid (3),
racemic 4-[3α,5α-peroxy-2β-(3-hydroperoxy-1-undecenyl)cyclopent-1α-yl]butanoic acid (3),
racemic 7-[3α,5α-peroxy-2β-(3-hydroperoxy-1-octenyl)-cyclopent-1α-yl]-5-heptenoic acid (3),
racemic 10-[3α,5α-peroxy-2β-(3-hydroperoxy-1-pentenyl)-cyclopent-1α-yl]-8-decenoic acid (3),
racemic 6-[3α,5α-peroxy-2β-(3-hydroperoxy-1-undecenyl)-cyclopent-1α-yl]hexanoic acid (3),
racemic 9-[3α,5α-peroxy-2β-(3-hydroperoxy-1-octenyl)-cyclopent-1α-yl]-7-nonenoic acid (3),
racemic 7-[3α,5α-peroxy-2β-(3-hydroperoxy-3-methyl-1-octenyl) cyclopent-1α-yl]heptanoic acid (3),
racemic 7-[3α,5α-peroxy-2β-(3-hydroperoxy-4-methyl-1-octenyl)-cyclopent-1α-yl]-heptanoic acid (3),
racemic 7-[3α,5α-peroxy-3β-methyl-2β-(3-hydroperoxy-3-methyl-1-octenyl)cyclopent-1α-yl]heptanoic acid (3),
racemic 7-[3α,5α-peroxy-1β,2α-dimethyl-2β-(3-hydroperoxy-1-octenyl)cyclopent-1α-yl]heptanoic acid (3) and
racemic 7-[3α,5α-peroxy-2β-(3-hydroperoxy-4,4-dimethyl-1-octenyl)cyclopent-1α-yl]-heptanoic acid (3), is productive of the corresponding acids of formula (4), for example:

racemic 8-[3α,5α-dihydroxy-2β-(3-hydroxy-1-octenyl)-cyclopent-1α-yl]octanoic acid (4),
racemic 6-[3α,5α-dihydroxy-2β-(3-hydroxy-1-pentenyl)-cyclopent-1α-yl]hexanoic acid (4),
racemic 5-[3α,5α-dihydroxy-2β-(3-hydroxy-1-octenyl)cyclopent-1α-yl]pentanoic acid (4),
racemic 8-[3α,5α-dihydroxy-2β-(3-hydroxy-1-pentenyl)-cyclopent-1α-yl]octanoic acid (4),
racemic 6-[3α,5α-dihydroxy-2β-(3-hydroxy-1-octenyl)-cyclopent-1α-yl]hexanoic acid (4),
racemic 6-[3α,5α-dihdroxy-2β-(3-hydroxy-1-octenyl)-cyclopent-1α-yl]-4-hexenoic acid (4),
racemic 4-[3α,5α-dihydroxy-2β-(3-hydroxy-1-undecenyl)-cyclopent-1α-yl]butanoic acid (4),
racemic 7-[3α,5α-dihydroxy-2β-(3-hydroxy-1-octenyl)-cyclopent-1α-yl]-5-heptenoic acid (4),
racemic 10-[3α,5α-dihydroxy-2β-(3-hydroxy-1-pentenyl)-cyclopent-1α-yl]-8-decenoic acid (4),
racemic 6-[3α,5α-dihydroxy-2β-(3-hydroxy-1-undecenyl)-cyclopent-1α-yl]hexanoic acid (4),
racemic 9-[3α,5α-dihydroxy-2β-(3-hydroxy-1-octenyl)-cyclopent-1α-yl]-7-nonenoic acid (4),
racemic 7-[3α,5α-dihydroxy-2β-(3-hydroxy-3-methyl-1-octenyl) cyclopent-1α-yl]heptanoic acid (4),
racemic 7-[3α,5α-dihydroxy-2β-(3-hydroxy-4-methyl-1-octenyl)-cyclopent-1α-yl]-heptanoic acid (4),
racemic 7-[3α,5α-dihydroxy-3β-methyl-2β-(3-hydroxy-3-methyl-1-octenyl)cyclopent-1αyl]heptanoic acid (4),
racemic 7-[3α,5α-dihydroxy-1β,2α-dimethyl-2β-(3-hydroxy-1-octenyl)cyclopent-1α-yl]heptanoic acid (4), and
racemic 7-[3α,5α-dihydroxy-2β-(3-hydroxy-4,4-dimethyl-1-octenyl)cyclopent-1α-yl]-heptanoic acid (4).

Example 10

Racemic 7-[3α-hydroxy-5-oxo-2β-(3-hydroxy-1-octenyl)cyclopent-1α-yl]heptanoic acid (racemic prostaglandin E$_1$) (5)

A solution of 0.15 p. of sodium borohydride in 3 ml. of 0.05N aqueous sodium hydroxide is added with stirring over a 15 min. period to a solution of 1.0 g. of racemic 7-[3α,5α-peroxy2β-(3-hydroperoxy-1-octenyl)cyclopent-1α-yl]heptanoate (3) in 25 ml. of isopropanol at room temperature (about 25°C) under nitrogen. Stirring is continued at room temperature for about an hour. The reaction mixture is then made acid with dilute aqueous hydrochloric acid, diluted with water, and evaporated under reduced pressure until the isopropyl alcohol is removed. The aqueous residue thus obtained is extracted with ethyl acetate and the ethyl acetate extract is washed with water, then with saturated aqueous sodium chloride, dried over sodium sulfate, and evaporated under reduced pressure to give a residue comprising racemic 7-[3α,5α-peroxy-2β-(3-hydroxy-1-octenyl)cyclopent-1α-yl]heptanoic acid (3a).

The thus obtained residue comprising racemic 7-[3α,5α-peroxy-2β-(3-hydroxy-1-octenyl)cyclopent- 1α-yl]heptanoic acid (3a) is dissolved in about 40 ml. of hexane and absorbed on 40 g. of slightly basic chromatographic alumina. The column is allowed to stand for about 5 hr., then is eluted with methanol and the eluate is evaporated to give a residue comprising racemic 7-[3α-hydroxy-5-oxo-2β-(3-hydroxy-1-octenyl)cyclopent-1α-y]-heptanoic acid (5). The residue is dissolved in a small amount of ethyl acetate and chromatographed over 100 g. of acid washed silica gel. The chromatogram is eluted with ethyl acetate containing increasing percentages of methanol and the eluate fractions are evaporated. The thus obtained residues are analyzed by thin layer chromatography to select the fractions comprising racemic 7-[3α-hydroxy-5-oxo-2β-(3-hydroxy-1-octenyl)cyclopent-1α-yl]heptanoic acid (5). The thus obtained product can be further purified by repeated chromatography, preparative thin layer chromatography, counter-current extraction, and crystallization, or by a combination of the above methods.

Following the procedure of Example 10 but substituting for racemic 7-[3α, α-peroxy-2β-(3-hydroperoxy-1-octenyl)cyclopent-1α-yl]heptanoic acid (3) as starting material other acids of formula 3, for example those named following Example 9, is productive of the corresponding acids of formula 5, for example: racemic 8-[3α-hydroxy-5-oxo-2β-(3-hydroxy-1-octenyl)-cyclopent-1α-yl]octanoic acid (5), racemic 6-[3α-hydroxy-5-oxo-2β-(3-hydroxy-1-pentenyl)-cyclopeht-1α-yl]hexanoic acid (5), racemic 5-[3α-hydroxy-5-oxo-2β-(3hydroxy-1-octenyl)-cyclopent-1α-yl]pentanoic acid (5), racemic 8-[3α-hydroxy-5-oxo-2β-(3hydroxy-1-pentenyl)-cyclopent-1α-yl]octanoic acid (5), racemic 6-[3α-hydroxy-5-oxo-2β-(3-hydroxy-1-octenyl)-cyclopent-1α-yl]hexanoic acid (5), racemic 6-[3α-hydroxy-5-oxo-2β-(3-hydroxy-1-octenyl)cyclopent-1αyl]-4-hexenoic acid (5)

racemic 4 -[3α-hydroxy-5-oxo-2β-(3-hydroxy-1-undecanyl)-cyclopent-1α-yl]butanoic acid (5), racemic 7-[3α-hydroxy-5-oxo-2α-(3-hydroxy-1-octenyl)-cyclopent-1αyl]-5-heptenoic acid (5), racemic 10-[3α-hydroxy-5-oxo-2β-(3-hydroxy-1-pentenyl)-cyclopent-1α-yl]-8-decenoic acid (5), racemic 6-[3α-hydroxy-5-oxo-2β-(3-hydroxy-1-undecenyl)-cyclopent-1α-yl]hexanoic acid (5), racemic 9-[3α-hydroxy-5-oxo-2β-(3-hydroxy-1-octenyl)-cyclopent-1α-yl]-7-nonenoic acid (5), racemic 7-[3α-hydroxy-5-oxo-2β-(3-hydroxy-3-methyl-1-octenyl)-cyclopent-1α-yl]heptanoic acid (5), racemic 7-[3α-hydroxy-5-oxo-2β-(3-hydroxy-4-methyl-1-octenyl)cyclopent-1α-yl]-heptanoic acid (5), racemic 7-[3α-hydroxy-5-oxo-3β-methyl -2β-(3-hydroxy-3-methyl-1-octenyl)cyclopent-1α-yl]heptanoic acid (5), racemic 7-[3α-hydroxy-5-oxo-1β,2α-dimethyl-2β-(3-hydroxy-1-octenyl)cyclopent-1α-yl]heptanoic acid (5), and racemic 7-[3α-hydroxy-5-oxo-2β-(3-hydroxy-4,4-dimethyl-1-octenyl)-cyclopent-1α-yl]-heptanoic acid (5).

Example 11

Racemic 7-[3α,5α-dihydroxy-2β-(2-octanyl)-cyclopent-1α-yl]heptanoic acid (8).

Following the procedure of Example 9 but substituting racemic 7-[3α,5α-peroxy-2β-(2-octenyl)-cyclopent-1α-yl]heptanoic acid (2) for racemic 7-[3α,5α-peroxy-2β-(3-hydroperoxy-1-octenyl)cyclopent-1α-yl]heptanoic acid (3) as starting material is productive of racemic 7-[3α,5α-dihydroxy-2β-(2-octenyl)-cyclopent-1α-yl]heptanoic acid (8).

Following the procedure of Example 9 but substituting for racemic 7-[3α,5α-peroxy-2β-(3-hydroperoxy-1-octenyl)cyclopent-1α-yl]heptanoic acid (3) as starting material compounds of formula 2, for example:

racemic 8-[3α,5α-peroxy-2β(2-octenyl)cyclopent-1α-yl]octanoic acid (2), racemic 6-[3α,5α-peroxy-2β-(2-pentenyl)cyclopent-1α-yl]-hexanoic acid (2), racemic 5-[3α,5α-peroxy-2β-(2-octenyl)cyclopent-1α-yl]-octanoic acid (2), racemic 8-[3α,5α-peroxy-2β-(2-pentenyl)cyclopent-1α-yl]-pentanoic acid (2), racemic 6-[3α,5α-peroxy-2β-(2-octenyl)cyclopent-1α-yl]-hexanoic acid (2), racemic 6-[3α,5α-peroxy-2β-(2-octenyl)cyclopent-1α-yl]-4-hexenoic acid (2), racemic 4-[3α,5α-peroxy-2β-(2-undecenyl)cyclopent-1α-yl]-butanoic acid (2), racemic 7-[3α,5α-peroxy-2β-(2-octenyl)cyclopent-1α-yl]-5-heptenoic acid (2), racemic 10-[3α,5α-peroxy-2β(2-pentenyl)cyclopent-1α-yl]-8-decenoic acid (2), racemic 6-[3α,5α-peroxy-2β-(2-undecanyl)cyclopent-1α-yl]-hexanoic acid (2), racemic 9-[3α,5α-peroxy-2β-(2-octenyl)cyclopent-1α-yl]-7-nonenoic acid racemic 7-[3α,5α-peroxy-2β(3-methyl- 2-octenyl)cyclopent-1α-yl]heptanoic acid (2), racemic 7-[3α,5α-peroxy-2β(4-methyl-2-octenyl)cyclopent-1α-heptanoic acid (2), racemic 7-[3α,5α-peroxy-3β-methyl-2β(3-methyl-2-octenyl)cyclopent-1α-yl]heptanoic acid (2), racemic 7-[3α,5α-peroxy-1β,2α-dimethyl-2β-(2-octenyl)-cyclopent1αyl]heptanoic acid (2), and racemic 7-[3α,5α-peroxy-2β-(4,4-dimethyl-2-octenyl)cyclopent-1αyl]-heptanoic acid (2), is productive of the corresponding compounds of formula 7, for example:

racemic 8-[3α,5α-dihydroxy-2β-(2-octenyl)cyclopent-1αyl]-octanoic acid (8), racemic 6-[3α,5α-dihydroxy-2β-(2-pentenyl)cyclopent-1α-yl]hexanoic acid (8), racemic 5-[3α,5α-dihydroxy-2β-(2-octenyl)cyclopent-1α-yl]-pentanoic acid (8), racemic 8-[3α,5α-dihydroxy-2β-(2-pentenyl)cyclopent-1α-yl]-octanoic acid (8), racemic 6-[3α,5α-dihydroxy-2β-(2-octenyl)cyclopent-1α-yl]-hexanoic acid (8), racemic 6-[3α,5α-dihydroxy-2β-(2-octenyl)cyclopent-1αyl]-4-hexenoic acid (8), racemic 4-[3α,5α-dihydroxy-2β-(2-undecenyl)cyclopent-1α-yl]-butanoic acid (8), racemic 7-[3α,5α-dihydroxy-2β-(2-octenyl)cyclopent-1α-yl]-3-heptenoic acid (8), racemic 10-[3α,5α-dihydroxy-2β-(2-pentenyl)cyclopent-1α-yl]-8-decanoic acid (8), racemic 6-(3α,5α-dihydroxy-2β-(2-undecanyl)cyclopent-1α-yl]-hexanoic acid (8), racemic 9-[3α,5α-dihydroxy-2β-(2-octenyl)cyclopent-1α-yl]-7-nonenoic acid (8), racemic 7-[3α,5α-dihydroxy-2β-(3-methyl-2-octenyl)-cyclopent-1α-yl]-heptanoic acid (8), racemic 7-[3α,5α-dihydroxy-2β(4-methyl-2-octenyl)-cyclopent-1α-yl]-heptanoic acid (8),
racemic 7-[3α,5α-dihydroxy-3β-methyl-2β-(3-methyl-2-octenyl cyclopent-1α-yl]heptanoic acid (8),
racemic 7-[3α,5α-dihydroxy-1β,2α-dimethyl-2β-(2-octenyl)cyclopent-1α-yl]heptanoic acid (8), and
racemic 7-[3α,5α-dihydroxy-2β(4,4-dimethyl-2-octenyl)cyclopent-1α-yl]-heptanoic acid (8).

Example 12A

Racemic 7-[3α-hydroxy-5-oxo-2β-(2-octenyl)cyclopent-1α-yl]heptanoic acid (6).

A solution of 1.0 g. of racemic 7-[3α,5α-peroxy-2β-(2-octenyl)cyclopent-1α-yl]-heptanoic acid (2) in a mixture of 20 ml. of isopropanyl and 5 ml. of pyridine is stirred under nitrogen and warmed to about 80°C. for a period of about 2 hrs. The mixture is then evaporated under reduced pressure to leave a residue which is then dissolved in ethyl acetate, and washed several times with dilute hydrochloric acid. The ethyl acetate solution is then washed with saturated aqueous sodium chloride, dried over sodium sulfate, and evaporated under reduced pressure to give a residue comprising racemic 7-[3α-hydroxy-5-oxo-2β-(2-octenyl)cyclopent-1α-yl]heptanoic acid (6). The thus obtained residue is dissolved in a small amount of ethyl acetate and chromatographed over 100 g. of acid washed silica gel. The column is eluted with ethyl acetate containing increasing percentages of methanol. The elute fractions are evaporated and the residues comprising racemic 7-[3α-hydroxy-5 -oxo-2β(2-octanyl)cyclopent-1α-yl]heptanoic acid are identified by TLC and infrared absorption analysis.

Following the procedure of Example 12A, but substituting for racemic 7-[3α,5α-peroxy-2β-(2-octenyl)-cyclopent-1α-yl ]heptanoic acid (2) as starting material other acids of formula (2), for example those named following Example 11, is productive of the corresponding acids of formula 6, for example:
racemic 8-[3α-hydroxy-5-oxo-2β-(2-octenyl)cyclopent-1α-yl]octanoic acid (6),
racemic 6-[3α-hydroxy-5-oxo-2β-(2-pentencyl)cyclopent-1α-yl]hexanoic acid (6),
racemic 5-[3α-hydroxy-5-oxo-2β-(2-octenyl)cyclopent-1α-yl]pentanoic acid (6),
racemic 8-[3α-hydroxy-5-oxo-2β-(2-pentenyl)cyclopent-1α-yl]-octanoic acid (6),
racemic 6-[3α-hydroxy-5-oxo-2β-(2-octenyl)cyclopent-1α-yl]hexanoic acid (6),
racemic 6-[3α-hydroxy-5-oxo-2β-(2-octenyl)-cyclopent-1α-yl]-4-hexenoic acid (6),
racemic 4-[3α-hydroxy-5-oxo-2β-(2-undecenyl)cyclopent-1α-yl]-butanoic acid (6),
racemic 7-[3α-hydroxy-5-oxo-2β-(2-octenyl)cyclopent-1α-yl]-5-heptenoic acid (6),
racemic 10-[3α-hydroxy-5-oxo-2β-(2-pentenyl)cyclopent-1α-yl ]-8-decenoic acid (6),
racemic 6-[3α-hydroxy-5-oxo-2β-(2-undecenyl)cyclopent-1α-yl]-hexanoic acid (6),
racemic 9-[3α-hydroxy-5-oxo-2β-(2-octenyl)cyclopent-1α-yl]-7-nonenoic acid (6),
racemic 7-[3α-hydroxy-5-oxo-2β-(3-methyl-2-octenyl)cyclopent-1α-yl]heptanoic acid (6),
racemic 7-[3α-hydroxy-5-oxo-2β-(4-methyl-2-octenyl)cyclopent-1α-yl]-heptanoic acid (6),
racemic 7-[3α-hydroxy-5-oxo-3β-methyl-2β-(3-methyl-2-octenyl)-cyclopent-1αyl]heptanoic acid (6),
racemic 7-[3α-hydroxy-5-oxo-1β,2α-dimethyl-2β-(2-octenyl)-cyclopent-1α-yl]heptanoic acid (6), and
racemic 7-[3α-hydroxy-5-oxo-2β-(4,4-dimethyl-2-octenyl)cyclopent-1α-yl]-heptanoic acid (6).

Example 12B

Racemic 7-[3α-hydroxy-5-oxo-2β-(2-octenyl)cyclopent-1α-yl]heptanoic acid (6).

A solution of 1 g. of racemic 7-[3α,5α-peroxy-2β-(2-octanyl)cyclopent-1α-yl]heptanoic acid (2) in about 40 ml. of hexane is adsorbed on 40 g. of slightly basic chromatographic alumina. The column is allowed to stand for about 5 hr., then is eluted with methanol and the eluate is evaporated to give a residue comprising racemic 7-[3α-hydroxy-5-oxo-2β-(2-octenyl)cyclopent-1α-yl]heptanoic acid (6). The thus obtained residue is dissolved in a small amount of ethyl acetate and chromatographed over 100 g. of acid washed silica gel. The column is eluted with ethyl acetate containing increasing percentages of methanol. The eluate fractions are evaporated and the residues comprising racemic 7-[3α-hydroxy-5-oxo-2β-(2-octenyl)cyclopent-1α-yl]heptanoic acid (6) are identified by TLC and infrared absorption analysis.

Following the procedure of Example 12B, but substituting for racemic 7-[3α,5α-peroxy-2β-(2-octenyl)cyclopent-1α-yl]heptanoic acid (2) as starting material other acids of formula (2), for example those named following Example 11, is productive of the corresponding acids of formula 6, for example those named following Example 12A.

Example 13

Racemic 7-[3α,5α-dihydroxy-2ββ-(3-hydroxy-1-octenyl)cyclopent-1α-yl]heptanoic acid (4) from racemic 7-[3α,5α-dihydroxy-2β-(2-octenyl)cyclopent-1α-yl]-heptanoic acid (8).

A. following the procedures of Examples 1 to 6, but substituting racemic 7-[3α,5α-dihydroxy-2β-(2-octenyl)cyclopent-1α-yl]heptanoic acid (8) for bish-omo-γ-linolenic acid as starting material there is obtained racemic 7-[3α,5α-dihydroxy-2β-(3-hydroperoxy-1-octenyl)cyclopent-1α-yl]-heptanoic acid (9).

Following the procedure of Example 13A, but substituting for racemic 7-[3α,5α-dihydroxy-2β-(2-octenyl)-cyclopent-1α-yl]heptanoic acid (8) as starting materia other acids of formula 8, for example those named following Example 11, is productive of the corresponding acids of formula 9, for example:
racemic 8-[3α,5α-hydroxy-2β-(3-hydroperoxy-1-octenyl)-cyclopent-1α-yl]octanoic acid (9),
racemic 6-[3α,5α-dihydroxy-2β-(3-hydroperoxy-1-pentenyl)-cyclopent-1αyl]hexanoic acid (9),
racemic 5-[3α,5α-dihydroxy-2β-(3-hydroperoxy-1-octenyl)-cyclopent-1α-yl]octanoic acid (9),
racemic 8-[3α,5α-dihydroxy-2β-(3-hydroperoxy-1-pentenyl)-cyclopent-1α-yl]pentanoic acid (9),
racemic 6-[3α,5α-dihydroxy-2β-(3-hydroperoxy-1-octenyl)-cyclopent-1α-yl]hexanoic acid (9),
racemic 6-[3α,5α-dihydroxy-2β-(3-hydroperoxy-1-octenyl)-cyclopent-1α-yl]-4-hexenoic acid (9),
racemic 4-[3α,5α-dihydroxy-2β-(3-hydroperoxy-1-undecenyl)-cyclopent-1α-yl]butanoic acid (9), racemic 7-[3α,5α-dihydroxy-2β-(3-hydroperoxy-1-octenyl)-cyclopent-1α-yl]-5-heptenoic acid (9), racemic 10-[3α,5α-dihydroxy-2β-(3-hydroperoxy-1-pentenyl)-cyclopent-1α-yl]-8-decenoic acid (9), racemic 6-[3α,5α-dihydroxy-2β-(3-hydroperoxy-1-undecenyl)cyclopent-1α-yl]hexanoic acid (9), racemic 9-[3α,5α-dihydroxy-2β-(3-hydroperoxy-1-octenyl)cyclopent-1α-yl]-7-nonenoic acid (9), racemic 7-[3α,5α-dihydroxy-2β-(3-hydroperoxy-3-methyl-1-octenyl) cyclopent-1α-yl]heptanoic acid (9), racemic 7-[3α,5α-dihydroxy-2β-(3-hydroperoxy-4-methyl-1-octenyl)cyclopent-1α-yl]-heptanoic acid (9), racemic 7-[3α,5α-dihydroxy-3β-methyl-2β-(3-hydroperoxy-3-methyl-1-octenyl)cyclopent-1α-yl]heptanoic acid (9), racemic 7-[3α,5α-dihydroxy-1β,2α-dimethyl-2β-(3-hydroperoxy-1-octenyl)cyclopent-1α-yl]heptanoic acid (9), and racemic 7-[3α,5α-dihydroxy-2β-(3-hydroperoxy-4,4-dimethyl-1-octenyl)cyclopent-1α-yl]-heptanoic acid (9).

B. Following the procedure of Example 9, but substituting racemic 7-[3α,5α-dihydroxy-2β-(3-hydroperoxy-1-octenyl)cyclopent-1α-yl]-heptanoic acid (9) for racemic 7-[3α,5α-peroxy-2β-(3-hydroperoxy-1-octenyl)cyclopent-1α-yl]heptanoic acid (3) as starting material is productive of racemic 7-[3α,5α-dihydroxy-2β-(3-hydroxy-1-octenyl)cyclopent-1α-yl]-heptanoic acid (4).

Following the procedure of Example 13B, but substituting for racemic 7-[3α,5α-dihydroxy-2β-(3-hydroperoxy-1-octenyl)cyclopent-1α-yl]-heptanoic acid (9) as starting material other compounds of formula 9, for example those named following Example 13A, is productive of the corresponding acids of formula 4, for example those named following Example 9.

Example 14

Racemic
7-[3α-hydroxy-5-oxo-2β-(3-hydroxy-1-octenyl)cyclopent-1α-yl]heptanoic acid (5) from racemic 7-[3α-hydroxy-5-oxo-2β-(2-octenyl)-cyclopent-1α-yl]heptanoic acid (6).

A. Following the procedures of Examples 1 to 6, but substituting racemic 7-[3α-hydroxy-5-oxo-2β-(2-octenyl)cyclopent-1α-yl]heptanoic acid (5) for bishomo-γ-llnoienic acid as starting material is productive of racemic 7-[3α-hydroxy-5-oxo-2β-(3-hydroperoxy-1-octenyl)cyclopent-1α-yl]heptanoic acid (7).

Following the procedure of Example 14A, but substituting for racemic 7-[3α-hydroxy-5-oxo-2β-(2-octenyl)cyclopent-1α-yl]heptanoic acid (6) as starting material other compounds of formula 6, for example those named following Example 12, is productive of the corresponding compounds of formula 7, for example:

racemic 8-[3α-hydroxy-5-oxo-2β-(3-hydroperoxy-1-octenyl)-cyclopent-1α-yl]octanoic acid (7), racemic 6-[3α-hydroxy-5-oxo-2β-(3-hydroperoxy-1-pentenyl)-cyclopent-1α-yl]hexanoic acid (7), racemic 5-[3α-hydroxy-5-oxo-2β-(3-hydroperoxy-1-octenyl)-cyclopent-1α-yl]pentanoic acid (7), racemic 8-[3α-hydroxy-5-oxo-2β-(3-hydroperoxy-1-pentenyl)-cyclopent-1α-yl]octanoic acid (7), racemic 6-[3α-hydroxy-5-oxo-2β-(3-hydroperoxy-1-octenyl)-cyclopent-1α-yl]hexanoic acid (7), racemic 6-[3α-hydroxy-5-oxo-2β-(3-hydroperoxy-1-octenyl)-cyclopent-1α-yl]-4-hexenoic acid (7), racemic 4-[3α-hydroxy-5-oxo-2β-(3-hydroperoxy-1-undecenyl)-cyclopent-1α-yl]butanoic acid (7), racemic 7-[3α-hydroxy-5-oxo-2β-(3-hydroperoxy-1-octenyl)-cyclopent-1α-yl]-5-heptenoic acid (7), racemic 10-[3α-hydroxy-5-oxo-2β-(3-hydroperoxy-1-pentenyl)-cyclopent-1α-yl]-8-decenoic acid (7), racemic 6-[3α-hydroxy-5-oxo-2β-(3-hydroperoxy-1-undecenyl)-cyclopent-1α-yl]hexanoic acid (7), racemic 9-[3α-hydroxy-5-oxo-2β-(3-hydroxperoxy-1-octenyl)-cyclopent-1α-yl]-7-nonenoic acid (7), racemic 7-[3α-hydroxy-5-oxo-2β-(3-hydroperoxy-3-methyl-1-octenyl)-cyclopent-1α-yl]heptanoic acid (7), racemic 7-[3α-hydroxy-5-oxo-2β-(3-hydroperoxy-4-methyl-1-octenyl)-cyclopent-1α-yl]-heptanoic acid (7), racemic 7-[3α-hydroxy-5-oxo-3β-methyl-2β-(3-hydroperoxy-3-methyl-1-octenyl)cyclopent-1αyl]-heptanoic acid (7), racemic 7-[3α-hydroxy-5-oxo-1β,2α-dimethyl-2β-(3-hydroperoxy-1-octanyl)cyclopent-1α-yl]heptanoic acid (7), and racemic 7-[3α-hydroxy-5-oxo-2β-(3-hydroperoxy-4,4-dimethyl-1-octenyl)cyclopent-1α-yl]-heptanoic acid (7).

B. A solution of 1.0 g. of racemic 7-[3α-hydroxy-5-oxo-2β-(3-hydroperoxy-1-octenyl)cyclopent-1αyl]-heptanoic acid (7) in a mixture of 20 ml. of ethanol and 5 ml. of glacial acetic acid is stirred at room temperature and 2 g. of zinc dust is added in portions over a period of about 15 minutes. The mixture is cooled to avoid a rise in temperature. After adding the zinc dust the mixture is stirred an additional 15 min., and then is filtered to remove solids. The filtrate is diluted with 40 ml. of water and the resulting mixture is concentrated until most of the ethanol is removed. The aqueous residue is then extracted with ethyl acetate and the ethyl acetate extract is washed with saturated aqueous sodium chloride, dried, and evaporated under reduced pressure to give a residue comprising racemic 7-[3α-hydroxy-5-oxo-2β-(3-hydroxy-1-octenyl)-cyclopent-1α-yl]heptanoic acid (5), which can be further purified as described above, e.g., in Example 9.

Following the procedure of Example 14B, but substituting for racemic 7-[3α-hydroxy-5-oxo-2β-(3-hydroperoxy-1-octenyl)cyclopent-1α-yl]heptanoic acid (7) as starting material other compounds of formula 7, for example those named following Example 14A, is productive of the corresponding compounds of formula 5, for example those named following Example 10.

We claim:

1. An optically active compound of the formula:

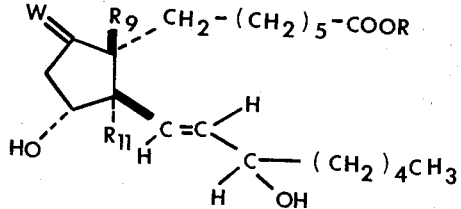

or a racemic compound of that formula and the mirror image thereof, wherein R is hydrogen or alkyl of 1 to 4 carbon atoms, inclusive, wherein W is

or O=, and wherein $R_9$ and $R_{11}$ are both alkyl of one to 4 carbon atoms, inclusive.

2. An optically active compound according to claim 1 wherein W is

3. A compound according to claim 2 wherein $R_9$ and $R_{11}$ are methyl.

4. A compound according to claim 3 wherein R is hydrogen.

5. An optically active compound according to claim 1 wherein W is O=.

6. A compound according to claim 5 wherein $R_9$ and $R_{11}$ are methyl.

7. A compound according to claim 6 wherein R is hydrogen.

* * * * *

UNITED STATES PATENT AND TRADEMARK OFFICE
CERTIFICATE OF CORRECTION

PATENT NO. : 3,953,499
DATED : Apr 27, 1976
INVENTOR(S) : John E. Pike et al.

It is certified that error appears in the above-identified patent and that said Letters Patent are hereby corrected as shown below:

Column 2, formula 4 should appear as follows:

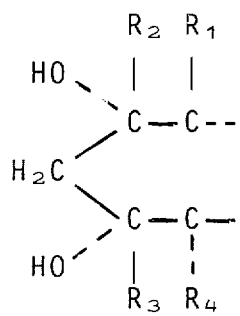

Column 2, formula 5 should appear as follows:

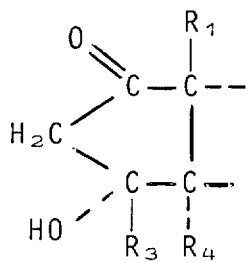

UNITED STATES PATENT AND TRADEMARK OFFICE
CERTIFICATE OF CORRECTION

PATENT NO. : 3,953,499
DATED : Apr 27, 1976
INVENTOR(S) : John E. Pike et al

It is certified that error appears in the above-identified patent and that said Letters Patent are hereby corrected as shown below:

Column 3, formula 4 should appear as follows:

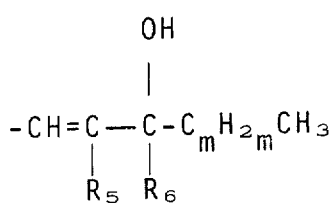

Column 3, formula 6 should appear as follows:

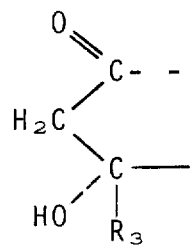

UNITED STATES PATENT AND TRADEMARK OFFICE
CERTIFICATE OF CORRECTION

PATENT NO. : 3,953,499
DATED : Apr 27, 1976
INVENTOR(S) : John E. Pike et al.

It is certified that error appears in the above-identified patent and that said Letters Patent are hereby corrected as shown below:

Column 3, formula 7 should appear as follows:

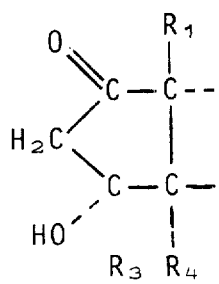

Column 8, lines 33-34: "$-CH_2-CH_2-$" should read as follows:
$\phantom{--}18\phantom{---}19$ -- $-CH_2-CH_2-CH_3$ --.
$\phantom{--}18\phantom{---}19\phantom{---}20$ Column 9, line 12: "as harmacological agents for pharmacological control" should read: --as pharmacological agents for the control--.

Column 10, line 64: "1-chloro-7,10,13-nonadecatrylyne" should read: --1-chloro-7,10,13-nonadecatriyne--.
Column 11, lines 17-18: "1-chloro-7,10,13-nonadecatrivne" should read: --1-chloro-7,10,13-nonadecatriyne--.
Column 12, line 29: 45 lb./sp. in." should read: --45 lb./sq. in--.
Column 13, line 49: "earth filter ald)" should read: --earth filter aid)--.

UNITED STATES PATENT AND TRADEMARK OFFICE
CERTIFICATE OF CORRECTION

PATENT NO. : 3,953,499
DATED : Apr 27, 1976
INVENTOR(S) : John E. Pike et al.

It is certified that error appears in the above-identified patent and that said Letters Patent are hereby corrected as shown below:

Column 13, line 55: "1-chloro-14-methylnonadeca-7,10-dlyn-13-ene" should read: --1-chloro-14-methylnonadeca-7,10-diyn-13-ene--.
Column 13, line 57: "Calc'd. for $C_{20}H_{21}Cl$:" should read: --Calc'd. for $C_{20}H_{31}Cl$:--.
Column 14, line 28: "15-methyl-8,11,14-alcosatrienoate" should read: --15-methyl-8,11,14-eicosatrienoate--.
Column 14, line 39: "15-Methyl-8,11,14-elcosatrienoic acid" should read: --15-Methyl-8,11,14-eicosatrienoic acid--.
Column 15, line 5: "2-Methyl-8,11,14-elcosatrienoic acid" should read: --2-Methyl-8,11,14-eicosatrienoic acid--.
Column 16, line 13: "($CH_2$-1 protone)," should read: --($CH_2$-1 protons),--.
Column 16, line 20: "2-Methyl-cis,cis,cis-8,11,14-elcosatrienoic acid" should read: --2-Methyl-cis,cis,cis-8,11,14-eicosatrienoic acid--.
Column 16, line 21: "A solution of 28 g." should read: --A solution of 2.8 g.--.
Column 19, line 42: "than with saturated" should read: --then with saturated--.
Column 22, line 10: "on the mixture" should read: --and the mixture--.
Column 23, line 64: "3N hydrochloric" should read: --2N hydrochloric--.
Column 26, line 12: "103M sodium" should read: --1.03M sodium--.
Column 26, line 54-55: "washed with silica gel" should read: --washed silica gel--.
Column 27, lines 11-13, 16-20: "-elcosatrienoic acid," should read: -- -eicosatrienoic acid,--.
Column 27, line 43: "-(2-undecanyl)" should read: -- -(2-undecenyl)--.
Column 27, line 45: "-1-undecanyl)-" should read: -- -1-undecenyl)- --.

UNITED STATES PATENT AND TRADEMARK OFFICE
CERTIFICATE OF CORRECTION

PATENT NO. : 3,953,499
DATED : Apr 27, 1976
INVENTOR(S) : John E. Pike et al.

It is certified that error appears in the above-identified patent and that said Letters Patent are hereby corrected as shown below:

Column 27, line 48: "-5-heptanoic" should read: -- -5-heptenoic--.
Column 27, line 52: "-8-decanoic" should read: -- -8-decenoic--.
Column 27, line 55: "-(2-undecanyl)" should read: -- -(2-undecenyl)--.
Column 27, line 57: "-1-undecanyl)-" should read: -- -1-undecenyl)- --.
Column 27, line 67: "7-[3α,5α-peroxy-2β-(2-octenyl)-cyclopent-" should read: --7-[3α,5α-peroxy-2β-(4-methyl-2-octenyl)cyclopent- --.
Column 27, line 68:
Column 28, line 1 : " 7-[3α,5α-peroxy-2β-(3-hydroperoxy-1-octenyl)-" should read: -- 7-[3α,5α-peroxy-2β-(3-hydroperoxy-4-methyl-1-octenyl)- --.
Column 28, line 30: "2,6-dl-t-butyl-p-cresol" should read: -- 2,6-di-t-butyl-p-cresol--.
Column 29, line 6: "$F_1$ )(4)." should read: -- $F_1\alpha$)(4).--.
Column 29, line 48: "-4-hexanoic acid" should read: -- -4-hexenoic acid--.
Column 30, line 10: "5-[3α,5α-dlhydroxy-2β-" should read: -- 5-[3α,5α-dihydroxy-2β- --.
Column 30, lines 12-13: "8-[3α,5α-dihydroxy-2β-(3-hydroxy-2β-(3-hydroxy-1-pentenyl)-cyclopent-1α-yl]octanoic acid" should read: -- 8-[3α,5α-dihydroxy-2β-(3-hydroxy-1-pentenyl)-cyclopent-1α-yl]octanoic acid--.
Column 30, line 49: "0.15 p. of sodium" should read: --0.15 g. of sodium--.

UNITED STATES PATENT AND TRADEMARK OFFICE
CERTIFICATE OF CORRECTION

PATENT NO. : 3,953,499
DATED : Apr 27, 1976
INVENTOR(S) : John E. Pike et al.

It is certified that error appears in the above-identified patent and that said Letters Patent are hereby corrected as shown below:

Column 31, lines 6-7: "7-[3α-hydroxy-5-oxo-2β-(3-hydroxy-1-octenyl)cyclopent-1α-y]-heptanoic acid" should read: --7-[3α-hydroxy-5-oxo-2β-(3-hydroxy-1-octenyl)cyclopent-1α-yl]-heptanoic acid--.

Column 31, line 21: "7-[3α, α-peroxy-" should read: --7-[3α,5α-peroxy- --.

Column 31, lines 41-42: "7-[3α-hydroxy-5-oxo-2α-(3-hydroxy-1-octenyl)-cyclopent-1αyl]-5-heptenoic acid" should read: 7-[3α-hydroxy-5-oxo-2β-(3-hydroxy-1-octenyl)-cyclopent-1α-yl]-5-heptenoic acid--.

Column 31, line 65: "7-[3α,5α-dihydroxy-2β-(2-octanyl)-cyclopent-" should read: --7-[3α,5α-dihydroxy-2β-(2-octenyl)-cyclo- --.

Column 32, line 29: "6-[3α,5α-peroxy-2β-(2-undecanyl)cyclopent-" should read: --6-[3α,5α-peroxy-2β-(2-undecenyl)cyclopent---.

Column 32, lines 35-36: "7-[3α,5α-peroxy-2β(4-methyl-2-octenyl)-cyclopent-1α-heptanoic acid" should read: --7-[3α,5α-peroxy-2β-(4-methyl-2-octenyl)cyclopent-1α-yl]-heptenoic acid--.

Column 32, lines 39-40: "7-[3α,5α-peroxy-1β,2α-dimethyl-2β-(2-octenyl)-cyclopentlαyl]-heptanoic" should read: --7-[3α,5α-peroxy-1β,2α-dimethyl-2β-(2-octenyl)-cyclopent-1α-yl]-heptanoic--.

Column 31, lines 39-40: "4-[3α-hydroxy-5-oxo-2β-(3-hydroxy-1-undecanyl)-cyclopent-" should read: 4-[3α-hydroxy-5-oxo-2β-(3-hydroxy-1-undecenyl)-cyclopent- --.

Column 32, lines 59-60: "7-[3α,5α-dihydroxy-2β-(2-octenyl)-cyclopent-1α-yl]-3-heptenoic" should read: --7-[3α,5α-dihydroxy-2β-(2-octenyl)-cyclopent-1α-yl]-5-heptenoic--.

Column 32, lines 61-62: "10-[3α,5α-dihydroxy-2β-(2-pentenyl)-cyclopent-1α-yl]-8-decanoic" should read: --10-[3α,5α-dihydroxy-2β-(2-pentenyl)-cyclopent-1α-yl]-8-decenoic--.

UNITED STATES PATENT AND TRADEMARK OFFICE
CERTIFICATE OF CORRECTION

PATENT NO. : 3,953,499

DATED : Apr 27, 1976

INVENTOR(S) : John E. Pike et al.

It is certified that error appears in the above—identified patent and that said Letters Patent are hereby corrected as shown below:

Column 32, line 63: "6-(3α,5α-dihydroxy-2β-(2-undecanyl)cyclo-" should read: --6-[3α,5α-dihydroxy-2β-(2-undecenyl)cyclopent- --.

Column 33, line 17: "20 ml. of isopropanyl" should read: --20 ml. of isopropanol--.

Column 33, line 33: "7-[3α-hydroxy-5-oxo-2β(2-octanyl)-cyclopent-" should read: --7-[3α-hydroxy-5-oxo-2β-(2-octenyl)-cyclopent- --.

Column 33, line 45: "6-[3α-hydroxy-5-oxo-2β-(2-pentencyl)cyclo-" should read: --6-[3α-hydroxy-5-oxo-2β-(2-pentenyl)-cyclopent- --.

Column 34, lines 12-13: "7-[3α,5α-peroxy-2β-(2-octanyl)-cyclopent-1α-yl]-heptanoic acid" should read: -- 7-[3α,5α-peroxy-2β-(2-octenyl)-cyclopent-1α-yl]heptanoic acid--.

Column 34, line 38: "7-[3α,5α-dihydroxy-2ββ-(3-hydroxy-1-octenyl)" should read: -- 7-[3α,5α-dihydroxy-2β-(3-hydroxy-1-octenyl)--.

Column 35, lines 49-50: "acid (5) for bishomo-λ-llnoienic acid" should read: --acid (6) for bishomo-λ-linolenic--.

UNITED STATES PATENT OFFICE
CERTIFICATE OF CORRECTION

Patent No. 3,953,499          Dated April 27, 1976

Inventor(s) John E. Pike et al.

It is certified that error appears in the above-identified patent and that said Letters Patent are hereby corrected as shown below:

Column 36, lines 22-23, "7-[3$\alpha$-hydroxy-5-oxo-1$\beta$,2$\alpha$-dimethyl-2$\beta$-(3-hydroxyperoxy-1-octanyl)-cyclopent-1$\alpha$-yl]heptanoic" should read --7-[3$\alpha$-hydroxy-5-oxo-1$\beta$,2$\alpha$-dimethyl-2$\beta$-(3-hydroxyperoxy-1-octenyl)-cyclopent-1$\alpha$-yl]heptanoic --.

Signed and Sealed this

Seventh Day of March 1978

[SEAL]

Attest:

RUTH C. MASON
Attesting Officer

LUTRELLE F. PARKER
Acting Commissioner of Patents and Trademarks